(12) United States Patent
Caillard et al.

(10) Patent No.: US 8,795,724 B2
(45) Date of Patent: Aug. 5, 2014

(54) MODIFIED PROTEIN EXCIPIENT FOR DELAYED-RELEASE TABLET

(75) Inventors: Romain Caillard, Quebec (CA);
Pierre-Louis Leclerc, Quebec (CA);
Muriel Subirade, Quebec (CA)

(73) Assignee: Universite Laval, Quebec (CA)

( * ) Notice: Subject to any disclaimer, the term of this patent is extended or adjusted under 35 U.S.C. 154(b) by 145 days.

(21) Appl. No.: 12/995,891

(22) PCT Filed: Jun. 11, 2009

(86) PCT No.: PCT/CA2009/000819
§ 371 (c)(1),
(2), (4) Date: Dec. 2, 2010

(87) PCT Pub. No.: WO2009/149553
PCT Pub. Date: Dec. 17, 2009

(65) Prior Publication Data
US 2011/0076326 A1    Mar. 31, 2011

Related U.S. Application Data

(60) Provisional application No. 61/060,849, filed on Jun. 12, 2008.

(51) Int. Cl.
*A61K 9/20* (2006.01)
*A61K 9/22* (2006.01)
*A61K 9/14* (2006.01)

(52) U.S. Cl.
USPC ........... 424/464; 424/465; 424/468; 424/491; 514/775

(58) Field of Classification Search
CPC ..... A61K 9/20; A61K 9/2063; A61K 9/2095; A61K 47/42; A61K 38/01
See application file for complete search history.

(56) References Cited

U.S. PATENT DOCUMENTS

| | | | | |
|---|---|---|---|---|
| 4,322,344 A | * | 3/1982 | Chen et al. | 530/378 |
| 4,401,682 A | * | 8/1983 | Battista | 426/285 |
| 4,401,683 A | * | 8/1983 | Thompson | 426/331 |
| 4,493,829 A | | 1/1985 | Sportoletti et al. | |
| 4,952,560 A | | 8/1990 | Kigasawa et al. | |

(Continued)

FOREIGN PATENT DOCUMENTS

WO    2007022239    2/2007

OTHER PUBLICATIONS

Zhao et al. Study of Succinylated Food Proteins by Raman Spectroscopy. J. Agric. Food Chem. 2004, 52, 1815-1823.*

(Continued)

*Primary Examiner* — Lakshmi Channavajjala
(74) *Attorney, Agent, or Firm* — Millen, White, Zelano & Branigan, PC

(57) ABSTRACT

The present invention relates to delayed release oral formulations comprising active ingredients and modified proteins used as excipients. The proteins have chemical modifications such as succmylation, deammation, glytarylation or phosphorylation which decrease the isoelectric point of the protein compared to the protein's native isoelectric point and enhance protem-protem interactions, thereby reducing solubility and swelling, and delaying release of the active ingredient when the formulation is ingested orally. Particularly, the invention relates to tablets that comprise an excipient of chemically-modified food proteins such as soy proteins or -lactoglobulm useful for delaying release of an active ingredient such as a pharmaceutical drug or a probiotic.

15 Claims, 16 Drawing Sheets

(56) References Cited

U.S. PATENT DOCUMENTS

| | | | |
|---|---|---|---|
| 5,212,235 | A | 5/1993 | Nestaas et al. |
| 5,656,296 | A * | 8/1997 | Khan et al. .................. 424/473 |
| 5,677,422 | A | 10/1997 | Safarian et al. |
| 5,939,091 | A * | 8/1999 | Eoga et al. .................. 424/441 |
| 5,986,050 | A | 11/1999 | Shalaby et al. |
| 6,048,562 | A | 4/2000 | Mandralis et al. |
| 6,399,086 | B1 | 6/2002 | Katzhendler et al. |
| 7,060,260 | B2 | 6/2006 | Fahnestock et al. |
| 2006/0193966 | A1 | 8/2006 | Wu et al. |
| 2007/0053869 | A1 | 3/2007 | Sugiyama et al. |

OTHER PUBLICATIONS

Young S. et al., 2005, "Gelatin as a delivery vehicle for the controlled release of bioactive molecules.", Journal of Controlled Release, 109: 256-274.

Singh M.P et al.,1995, "The Effect of Electrostatic Charge Interactions on Release Rates of Gentamicin from Collagen Matrices.", Pharmaceutical Research, vol. 12, No. 8.

GMIA, 2009, "Raw Materials & Production.", Found in Gelatin Manufactureres Institute of America: www.gelatin-gmia.com/html/rawmaterials_app.html.

Subirade et al., 2008, "Food-protein-derived materials and their use as carriers and delivery systems for active food components.", Woodhead Publishing Limited.

Phillips L. G. and Kinsella J.E. et al., 1990, "Effects of Succinylation on B-Lactoglobulin Foaming Properties.", Journal of Food Science, vol. 55, No. 6.

Kinsella J.E. et al., 1976, "Functional Properties of Succinylated and Acetylated Soy Protein.", J. Agri. Food Chem., vol. 24, No. 4.

Guegen et al., 1993, "Influence f the dissociation on the surface behaviours of oligomeic seed storage proteins: the example of pea legumin." Food Proteins: Structure and Functionality, ed. K.D. Schenke and R. Mothes, VH Weinheim (FRG) 281-289.

Schwenke K.D. et al., 1993, "Modification of the structure of 11S globulins from plant seeds by succinylation.", Food Proteins: Structure and Functionality, ed. K.D. Schwenke and R. Mothes, VCH Weinheim (FRG), 143-153.

Hwang D.C. & Damodaran S., 1996, "Chemial modification strategies for synthesis of protein-based hydrogel.", Journal of Agriculture and Food Chemistry, 44: 751-758.

Klayraung S. et al., 2009, "Development of tablets containing probiotics: Effects of formulation and processing parameters on bacterial viability.", International Journal of Pharmaceutics, 370: 54-60.

Vaz C.M. et al., 2003, "Soy Matrix Drug Delivery Systems Obtained by Melt Processing Techniques.", JOB, Aug. 8, 2003.

Chen L. et al., 2006, "Food Proteins based materials as nutraceutical delivery systems.", Trend in Food Science & Technology, 17: 272-283.

Vaz C.M. et al., 2003, "Development and design of double-layer co-injection molded soy protein, based drug delivery devices.", Polymer, 44:5983-5992.

Subirade M. et al., 1992, "Effect of dissociation and conformational changes on the surface behaviour of Pea Legumin.", J. Collod Internface Sci., 152: 442-454.

Sing M.P. et al., 1995, "The effect of electrostatic charge interactions on release rates of Gentamicin from collagen matrices.", Pharmaceutical research, vol. 12, No. 8: 1205-1210.

Achouri A. et al., 1998, "Enzymatic hydrolysis of soy protein isolate and effet succinylation on the functional properties of resulting protein hydrolyzates.", Food Research International, vol. 31, No. 9: 617-623.

Gruener L. & Ismond H., 1997, "Effects of acetylation and succinylation on the physichochemical properties of the canola 12S globulin", Part I, Food Chemistry, vol. 60, No. 3: 357-363.

Achouri A. & Zhang W., 2001, "Effect of succinylation on the physiochemical properties of soy protein hydrolyzate.", Food Research International, 34: 507-514.

El-Adawy T., 2000, "Functional properties and nutritional quality of acetylated and succinylated mung bean protein isolate.", Food Chemistry, 70: 83-91.

Gruener & Ismond, 1997, "Effects of acetylation and succinylation on the functional properties of the canola 12S globulin", Food Chemistry, vol. 60, No. 4, 513-520.

Georget D.M.R. et al., 2008, "A study on maize proteins as a potential new tablet excipient." European Journal of Pharmaceutics ans Biopharmaceutics, 69: 718-726.

Poulin J.-F. et al., 2011, "B-Lactoglobulin tablets as a suitable vehicle for protection and intestinal delivery of probiotic bacteria.", International Journal of Pharmaceutics, 405: 47-54.

Sriamornsak P. et al., 2007, "Swelling and erosion of pectin matrix tablets and their impact on drug release behavior.", European Journal of Pharmaceutics and Biopharmaceutics, 67: 211-219.

Supplementary European Search Report issued on Nov. 26, 2013 in corresponding European Patent Application No. 09761211.3, 11 pages.

Caillard, R., et al., "Characterization of Amino Cross-Linked Soy Protein Hydrogels," Journal of Food Science, vol. 73, No. 5, 2008, pp. C283-C291.

* cited by examiner

◆ 0%; ▲ 50%; ■ 100%

◆ 0%; ▲ 50%; ■ 100%

♦ 0%; ▲ 50%; ■ 100%

♦ 0%; ▲ 50%; ■ 100%

◆ 0%; ▲ 50%; ■ 100%

◆ 0%; ▲ 50%; ■ 100%

MODIFIED PROTEIN EXCIPIENT FOR DELAYED-RELEASE TABLET

CROSS-REFERENCE TO RELATED APPLICATIONS/PRIORITY CLAIM

This application is a national phase of PCT patent application serial number PCT/CA2009/000819, filed Jun. 11, 2009, designating the United States of America, now pending, THE SPECIFICATION of which IS hereby incorporated by reference, AND which claims benefit of U.S. Provisional application No. 61/060,849, filed Jun. 12, 2008.

FIELD OF THE INVENTION

The present invention relates to the delayed release of molecules when formulated in a compressed tablet that is protein-based of which the protein's isoelectric point has been modified in order to reduce solubility and swelling. Particularly, the invention relates to tablets that comprise an excipient comprising chemically-modified food proteins such as soy proteins or β-lactoglobulin useful for delaying release of an active ingredient, namely a pharmaceutical drug or a probiotic.

BACKGROUND

Food proteins are widely used in formulated foods because of their nutritional value and functional properties, including emulsifying, foaming, gelling, and water-binding capacities. However, their use in other fields, including pharmaceutical applications is still limited since few works have studied the drug-release properties of food protein-based systems (Chen et al. 2006).

In previous studies, it was shown that release properties of protein based-delivery systems are largely influenced by their matrix swelling properties. Peppas et al. (2000) report that according to the Flory-Rhener theory (1943), swelling is dependent on three components: mixing forces, ionic forces, and elastic forces. Mixing forces are dependent on polymer affinity for release media (which could be linked to polymer solubility), ionic forces are dependent on protein charge (the more the protein is charged, the higher the swelling rate) and elastic forces are connected to interactions between polymer chains that oppose to swelling phenomenon: the higher the cross-linking in the system, the lesser the swelling.

Therefore, modulation of one or more of these mechanisms may possibly lead to a control of the rate of release of a drug from a drug-excipient system or achieve targeting to a particular organ (for example: gastro-resistance favoring intestinal release).

An aspect of this invention provides a strategy allowing to slow down one (or more) of these mechanisms in order to provide a controlled-release system of a protein-based compressed 3-dimensional system or matrix, such as, for example, a tablet.

SUMMARY OF THE INVENTION

Therefore, the present invention relates to an excipient for use in delayed-release of an active ingredient. Particularly, the invention relates to a pharmaceutically acceptable excipient which is protein-based. More particularly, the excipient is a modified protein which has decreased isoelectric point when modified compared to its original pI when non-modified, thereby diminishing its solubility at low pH (such as in the stomach) and having higher solubility at higher pH (such as in the gut). Most particularly, the excipient is a modified protein which has decreased swelling when pressed, in a 3-dimensional system, thereby prolonging the time of release of an active ingredient mixed therewith.

The present invention also relates to a 3D-system comprising: /consisting essentially of: /consisting of: an active ingredient in combination with an excipient comprising/consisting essentially of: /consisting of: a protein having a modified pI below its original pI when non-modified such as to form a matrix for the delayed-release of said active ingredient when said protein is pressed in a 3-dimensional system.

The present invention further relates to a method for the manufacture of a delayed-release of an active ingredient in admixture with a protein excipient, said method comprising the steps of:

modifying a protein excipient in order to diminish its original isoelectric point (pI);
mixing said excipient with the active ingredient;
pressing said mixture;
whereby said excipient, when formulated in a pressed 3-D system, induces delayed-release of said active ingredient in the stomach while being released in the gut (i.e. gastro-resistance).

In a fourth aspect, the present invention provides for the use of a modified protein as defined herein for the manufacture of a 3-dimensional system for the delayed administration of a oral drug.

In a fifth aspect, the invention provides a modified protein as defined herein for use as an excipient in admixture with a active ingredient.

DESCRIPTION OF THE INVENTION

Figure 1:
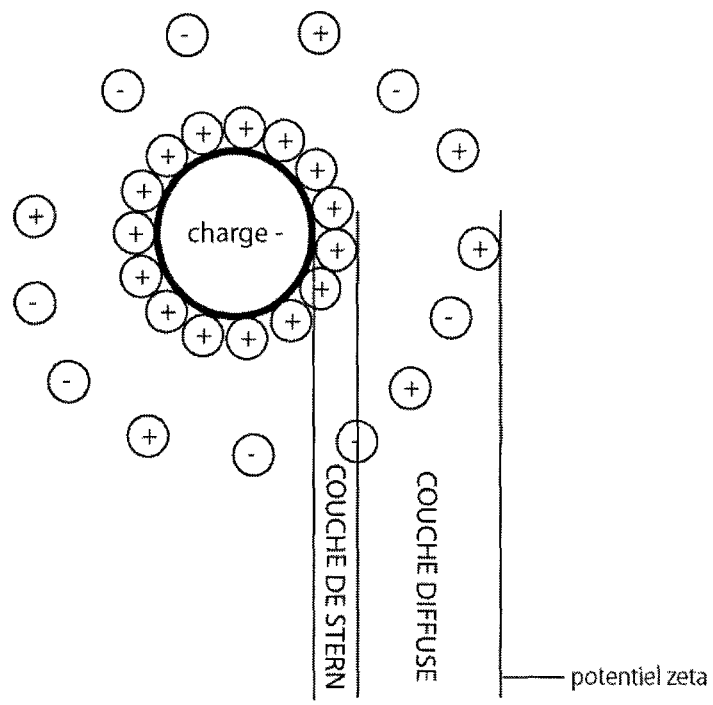
FIG. 1: Illustration of zeta potential.

For the purpose of the present invention the following terms are defined below.

DEFINITIONS

The terms "3-dimensional system" or "3-D system", as used herein, means a tablet, a pellet, a granule, a lozenge, a pill, a capsule or a caplet made out of protein or proteinic material that is pressed and results in a solid matrix.

The term "active ingredient" as used herein means any chemical or biological substance that has a physiological effect in human or in animals, when exposed to it.

The term "excipient" as used herein means any inert substance such as a powder or liquid, that forms a vehicle for an active substance, such as for example, a drug. Other excipient may include any known substance known in the pharmaceutical industry to modulate or modify the technological properties of powder such as for example, diluents, agglutinants, binders, lubrifiers or disintegrants, etc.

The term "pI modification" as used herein means any known chemical reaction allowing a decrease of isoelectric point of a protein, such as for example, succinylation, acetylation, octenyl-succinylation, glutarylation, phosphorylation and EDTAD.

The term "protein" or "proteinic material" as used herein means that the material originates from proteinic material either from animal or plant origin (vegetable and cereals), but may be native or in an altered state such as, but not limited to, pre-treated and/or denatured and/or hydrolyzed. Particular proteins used in the present invention are globular proteins, particularly food proteins.

The term "pressed" is used herein interchangeably with the expressions "compressed", "compacted", "extruded", "packed", "condensed", "agglomerated", or "aggregated", or any other such word that may mean pressed together to form a packed unit, form or matrix, such as, for example, a tablet, a granule, a pellet, a pill, a lozenge, a capsule or a caplet.

The abbreviation "SGF" as used herein means "simulated gastric fluid" and consist of 2 g of sodium chloride, 7 mL of 37% hydrochloric acid, 1000 mL of HPLC grade water (pH 1.2) and pepsin (3.2 g, 924 units/mg of protein) as defined in *US pharmacopoeia* (*The United States Pharmacopoeial Convention, Tests Solutions*, USP Convention Inc., Rockville, Md., 2004, pp. 9-23).

The abbreviation "SIF" as used herein means "simulated intestinal fluid" and is obtained by combining 6.8 g of monobasic potassium phosphate dissolved in 250 mL of HPLC grade water, 190 mL of 0.2 N sodium hydroxide and 400 mL of HPLC grade water. The pH was adjusted to 7.5±0.1 using 0.2 N sodium hydroxide, and the final volume was then brought to 1000 mL with double-distilled water. Pancreatin was added (10 g, activity equivalent to USP specification), as defined in *US pharmacopoeia* (*The United States Pharmacopoeial Convention, Tests Solutions*, USP Convention Inc., Rockville, Md., 2004, pp. 9-23).

DETAILED DESCRIPTION OF PARTICULAR EMBODIMENTS

A particular aspect of the invention relates to a plant or animal protein, particularly food proteins (including dairy proteins such as whey protein extract or whey protein isolate). Particularly, the protein is from plant origin including leguminous or cereal (grain) or vegetable protein. More particularly, the protein is from leguminous or cereal (grain) protein. Most particularly, the protein is a globular protein, even most particularly soy proteins are used in the form of soy protein isolate or soy protein extract or any other form known in the art. Alternatively, β-lactoglobulin is used.

A further aspect of the invention relates to a protein wherein the isoelectric point is decreased through chemical modification. Particularly, the modification of the protein pI is carried out by any means known in the art, including but not limited thereto, chemical modification suitable for adding acid groups to a protein, for blocking or neutralizing basic groups, for deamination, or combinations thereof.

Particularly, addition of acid groups on a protein may be carried out by grafting carboxylic groups or phosphoric groups. Alternatively, blocking or neutralizing basic groups may be carried out by blocking or neutralizing amine groups. Alternatively, deamination of the protein may be carried out by transforming glutamine to glutamic acid, asparagines to aspartic acid, etc. All methods mentioned hereinabove are extremely well known in the art, such as, for example: methylation, acetylation, phosphorylation, sulfation, carboxylation, arylation, alkylation, deamidation, succinylation, acetylation, glutarylation, octenyl-succinylation, reaction with EDTAD, reaction with anhydride, reaction with fluorescein isothiocyanate, or reaction with dimethylaminonaphtylsulfonyl chloride (dansyl chloride).

Most particularly, the protein's pI is modified through succinylation (Subirade et al., 1992; Schwenke et al., 1992), acetylation (Gruener L. and Ismond H., 1997), octenyl-succinylation, phosphorylation, glutarylation (Singh M. P. et al., 1995), or modification by Ethylene Diamine Tetra Acetic Dianhydride (EDTAD) (Hwang D-C., Damodaran S., 1996). More particularly, the protein is modified through succinylation, octenyl-succinylation, or glutarylation.

Even more particularly, the protein is modified at between 1% and 100% of its available sites, more particularly between 5% and 100%, even more particularly, between 10 and 100%, most particularly between 15% and 100%. Still particularly, between 25% and 100% of the available sites on the protein are modified, more particularly, between 50 and 100%, most particularly between 75% and 100%. Most particularly, the protein is 75% modified. Still, most particularly, the 100% of the available sites on the protein are modified.

The present invention particularly relates to an excipient for use in a delayed release 3-D system or matrix, said excipient comprising: /essentially consisting of: /consisting of: soy proteins having a modified isoelectric point (pI) below 4.5 wherein said soy protein is to be formulated in a compressed 3-D system such that protein-protein interactions are enhanced by said pI modulation and compression, thereby reducing swelling and delaying release of said active ingredient when ingested by a subject. Particularly, with respect to soy proteins, the modified isoelectric point (pI) between 4.4 and 3.5 wherein said excipient is to be formulated in a compressed 3-D system such that protein-protein interactions are enhanced by said pI modulation and compression, thereby reducing 3-D system swelling and delaying release of said active ingredient when ingested by a subject.

The present invention thereby relates to a 3-D system comprising: /consisting essentially of: /consisting of: an active ingredient in combination with an excipient essentially consisting of soy proteins having a modified pI between 4.4 and 3.5 such as to form a matrix for the delayed-release of said active ingredient when said protein is compressed in a 3-D system.

The present invention also relates to an excipient for use in a delayed release tablet comprising soy proteins having a modified isoelectric point (pI) below 4.5, particularly between 4 and 3.5, wherein said excipient is to be formulated in a compressed tablet such that protein-protein interactions are enhanced by said pI modulation and compression and thereby reduces tablet swelling and release of said active ingredient. Particularly, pI is between 3.9 and 3.6. More particularly, the pI is between 3.8 and 3.7.

The present invention particularly relates to an excipient for use in a delayed release 3-D system, said excipient comprising: /essentially consisting of: /consisting of: β-lactoglobulin having a modified isoelectric point (pI) below 5.2 wherein said β-lactoglobulin is to be formulated in a compressed 3-D system such that protein-protein interactions are enhanced by said pI modulation and compression, thereby reducing swelling and delaying release of said active ingredient when ingested orally by a subject. Particularly, with respect to β-lactoglobulin, the modified isoelectric point (pI) between 5.1 and 3.0 wherein said excipient is to be formulated in a compressed 3-D system such that protein-protein interactions are enhanced by said pI modulation and compression, thereby reducing swelling and delaying release of said active ingredient when ingested orally by a subject.

The present invention thereby relates to a tablet comprising: /consisting essentially of: /consisting of: an active ingredient in combination with an excipient consisting of β-lactoglobulin having a modified pI between 4.8 and 3.3 and said protein is compressed such as to form a tablet suitable for the delayed-release of said active ingredient when ingested orally in a subject.

The present invention also relates to an excipient for use in a delayed release tablet comprising whey protein extract or whey protein isolate, or even particularly β-lactoglobulin, having a modified isoelectric point (pI) below 5.2, particularly between 5.1 and 3.0, wherein said excipient is to be formulated in a compressed/compacted tablet such that protein-protein interactions are enhanced by said pI modulation and compression and thereby reduces tablet swelling and release of said active ingredient. Particularly, pI is between 4.8 and 3.3. More particularly, the pI is between 4.6 and 3.4.

The present invention further relates to a method for the manufacture of a delayed-release of an active ingredient comprising the steps of:

modifying a protein excipient in order to diminish its original isoelectric point (pI);
mixing the modified protein with an active ingredient to obtain a homogeneous mixture; and compressing said mixture to form a 3-D system;

whereby said excipient, when formulated in a compressed 3-D system, induces delayed release of said active ingredient when ingested orally in a subject.

Particularly, the modified protein and the active ingredient may be further mixed with one or more other excipients before pressing.

Particularly, the homogenous mixture is compressed by any means well know in the art such as, for example, by way of extrusion, pelletization, pressing, etc. Instruments suitable for such compaction may be chosen from extruder, press, rotating drums, pelletizing drum or disk, rotating mill, etc.

Particularly, when using a press, the pressure applied to form said 3-D system or matrix is any pressure sufficient to achieve the formation of a solid form, such as a tablet. Particularly, presses used to achieve a tablet will have a minimal pressure of about 30 MPa (1000 lbs) but any pressure achieving a solid tablet is suitable. Particularly, the pressure applied to said tablet is between 4000 and 18000 pounds, more particularly between 6000 and 14000 pounds; still more particularly, between 7000 and 10000 pounds; even more particularly between 8000 and 9000, most particularly around 9000 pounds. For convenience purposes, 18,000 lbs means 9 tons which is equivalent to about 8,200 kg, or about 87,400 PSI, or about 6020 bars.

Particularly, the pressure applied to form the 3-D system is applied for as much time as needed to achieve the formation of a solid form. Particularly, usual presses will compact the powder for at least about 30 sec but any length of time below that time is also suitable. Particularly, the tablet is pressed for about 30 sec to 5 minutes; particularly for 30 sec to 4 minutes; even more particularly between 1 to 3 minutes, most particularly around 1.5 minute.

Particularly, the ratio between excipient and active ingredient in the 3-D system is from 99.9:0.1 to 1:99, more particularly from 90:10 to 10:90. Most particularly, the ratio is from 80:20 to 20:80; from 70:30 to 30:70; from 60:40 to 40:60; or 50:50.

Generally the excipient is present in the 3-D system at a greater amount than the active ingredient. Particularly, the ratio is between 99:1 to 30:70. More particularly, the ratio is between 95:5 to 50:50, or between 95:5 to 40:60; between 90:10 to 70:30; between 90:10 to 80:20. However, the active ingredient may be present in as much as about 60% of the total mass of the tablet.

Particularly, the 3-D system or matrix may be selected from: tablets, granules, pellets, capsules, lozenges, pills, caplets, etc.

Particularly, the subject may be human or animal. Preferably, the subject is human, fish, farm animal or pets (such as cats, dogs, horses, pigs, and most monogastric mammals). More particularly, the subject is human.

Particularly, the excipient of the present invention may be used in admixture with one or more of the following active ingredients such as, for example: antiagreggants, antiangiogenics, antiarrythmia, antibiotics, antidepressors, antifungals, antivirals, anticholinergics, antiepileptics, anticoagulants, anticonvulsives, antidiarrheas, antihistaminics, antihypertensives, antiinflammatory, analgescis, antalgics, antipsychotics, antispasmodics, synthetic antithyroïds, anxiolytics, beta-bloquers, cardiotonics, diuretics, hypnotics, hypoglycemics, hypolipemics, inhibitors of conversion enzyme, inhibitors of angiotensin II, interferon, mucolytics, nootropics, phényléthylamines, sartans, triptans, etc. . . . but also neutraceuticals such as, for example: vitamins, flavonoïds, prebiotics, probiotics, minerals, ellagic acid, fatty acids ω3, fatty acids ω6, terpenes, etc.

Particularly, in the present study, in order to form soy protein tablets with modified release properties, a chemical strategy, based on the Flory-Rhener theory, was set up. Thus, in order to modulate protein tablets release properties, soy proteins succinylation was envisaged.

Succinylation is a chemical reaction consisting in adding carboxylic groups on proteins amino groups by a nucleophilic attack and thus allow to substitute a negative charge at a positively charge lysine group:

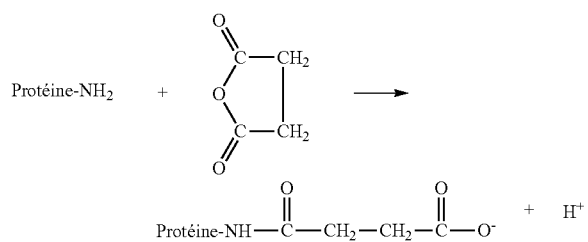

Scheme 1: Reaction of Succinic Anhydride with a Proteinic Amine Group
(see Schwenke, K. D. et al., 1993; Subirade, M. et al. 1992; and Gueguen, J. et al., 1993).

This modification was already used in food research area in order to increase soy proteins emulsifying and foaming properties (Gruener and Ismond, 1996, Achouri et al., 1998, Achouri et al., 2000, El-Adawy, 2000). Protein succinylation leads to protein unfolding and a decrease of protein isoelectric point (pI) leading to a decrease of protein solubility below its pI and an increase of protein solubility above its pI (Gruener and Ismond, 1996, Achouri et al., 1998, Subirade et al. 1992). Consequently, succinylation was thought to be an interesting chemical modification in order to modulate properties of protein-based systems for drug delivery. Moreover, succinylation is thought to be a very soft modification, even in foods. Indeed, succinic anhydride is already used in the Canadian food industry in the chemical modification of starch (Health Canada, 2004.

The impact of succinylation on the solubility of proteins and their charge on a pH basis, as well as their secondary structure, have been studied. The results obtained confirm those observed in the literature for emulsifying and foaming properties that an increase in the rate of succinylation leading to modifications of the structure II of the proteins, leads to a decrease of the isoelectric point of the proteins, a decrease of the zeta potential (surface charge) for acid pH's/an increase for alkaline pH's, as well as to a decrease of the solubility for acid pH's/an increase for alkaline pH's.

We used these properties to our advantage in the new application in that compressed tablets made from succinylated proteins show decreased swelling under acid pH and increased swelling under alkaline pH. The figures presented herein illustrate release profiles obtained when carrying out in vitro dissolution tests in simulated gastric and intestinal fluids (The United States Pharmacopeial Convention, 2004). Two tracers were used: riboflavin (vitamin B2), soluble, and rifampicin (antibiotic) of low solubility.

The results obtained show that, notwithstanding the active ingredient under study, the compressed/compacted tablets formed from succinylated proteins have a significant decrease in drug release under simulated gastric conditions (less than 15% released after 6 h) and significant increase in drug release under intestinal conditions. Taking into account that the gastric passage varies between thirty minutes (fasting individual) and four hours (individual having eaten a caloric meal) (Ewe et al., 1991), it appears that this type of formulation provides gastro-resistance and a targeted release in intestinal media.

EXAMPLES

Example 1

Materials

The soybean isolate SPI 6000 used in the present study was a gift from Protient Inc. (Saint Paul, Minn.). Succinic anhydride was obtained from Fisher Scientific Inc. (Springfield, N.J.). Enzymes and other chemicals used for dissolution experiments were obtained from Sigma Chemical Co. (Saint Louis, Mo.). BCA (Bicinchoninic Acid) reaction kit was obtained from Pierce (Rockford, Ill.). Dialysis membrane were obtained from SpectrumLabs (Houston, Tex.). Tablets photographs were taken using a Canon Power Shot A75 camera (Canon Inc., Japan).

Chemical Modification of Soy Proteins

Soy protein modification was carried out as follows. Soy proteins were dispersed in water for 2 h at a concentration of 5%. Small amounts of succinic anhydride were added to soy protein solutions with constant stirring. During reaction, pH was maintained at between 8 and 8.5 with NaOH 2M. After the pH stabilized, the suspensions were dialyzed for one night at 4° C. (pore size 1000 Da) and were then lyophilized and crushed in powder. The extent of succinylation of amino groups was controlled using the OPA (OrthoPhtadiAldehyde) method. The OPA reagent was prepared daily by mixing 80 mg of OPA (dissolved in 2 mL of methanol), 100 mL of 0.1 mol/L sodium borate buffer, pH 9.3, 200 µL of β-mercaptoethanol and 2.5 mL of SDS 20%. 0.7% of modified and unmodified soy protein solutions and aliquots of 150 L were placed in 3 mL reagent cuvettes, mixed with reagent and left at room temperature for 15 min. Absorbance at 340 nm was measured. A blank was prepared identically. A standard curve with L-Leucine was prepared for concentrations between 0.75 mM and 3 mM. The extent of succinylation was calculated as the percentage of lysine that reacted with the succinic anhydride (% reacted lysine) as follows:

% Reacted lysine=$[(Lys_C-Lys_R)/Lys_C]\times 100$ where $Lys_C$ is the concentration of reactive lysine in unmodified soy protein solution and $Lys_R$ is the concentration of reactive lysine in modified soy protein solutions. All measurements were performed in triplicate.

FTIR Spectroscopy

Soy protein secondary structure was studied using FTIR spectroscopy. Succinylated soy protein solution were prepared as follows: a 5% soy protein solution of modified and unmodified protein was prepared in $D_2O$ by mixing for about three hours at room temperature using a magnetic stirrer under an $N_2$ atmosphere. After 24 h, infrared spectra were recorded with a Magna 560 Nicolet spectrometer (Madison, Wis.) equipped with mercury-cadmium-telluride detector. The spectrometer was continuously purged with dried air. Thin slices of gel were placed between two $CaF_2$ windows separated by 23-µm polyethylene terephthalate film spacers. Each spectrum is the result of an average of 128 scans and apodized with a Happ-Genzel function. To study the amide I region of the protein (the so-called amide I' in deuterated peptide groups), subtractions and Fourier self-deconvolutions (to identify each overlapping component under the amide I' region) were performed using the software provided with the spectrometer (Omnic software). Band narrowing was achieved with a full width at half of 24 cm$^{-1}$ and with a resolution enhancement factor of 2.5 cm$^{-1}$.

Proteins Zeta Potential Measurements

Zeta potential measurements were conducted using a Zetasizer 2000 (Malvern instruments, Worcesterhire, UK). Zeta potential is a measure of the net charge on a particle and depends on the charge on the particle plus the charge of associated with any ions that move along with the particle in an electric field (see FIG. 1). In order to study succinylation impact on protein zeta potential, 0.1% proteins solutions were prepared in 10 mM buffers. Before injecting protein samples, the pH of each solution was measured. An 150V/cm potential was applied and the time measurement was set to 20 s. For each modification rate, zeta potential was scaled to the pH. Each measurement was conducted four times.

Protein Solubility Evaluation

Succinylation impact on protein solubility was approximated using a modified NSI method (Nitrogen Solubility Index, AOCS specification Ba 11-65) where Kjeldahl dosage was replaced by a BCA reaction (Bicinchoninic Acid). Proteins were dispersed in 100 mM buffers at a concentration of 2% at room temperature for 2 h. Protein solutions were then centrifuged at 1500 rpm for 10 min. Proteins solution aliquots of 200 µL were placed in 5 mL tubes, mixed with 4 mL of BCA reagent and left at 37° C. for 30 min. Absorbance at 562 nm was measured for protein solution before centrifugation and for supernatant. A blank was prepared identically. Absorbance was converted in protein concentration and scaled to the pH. A standard curve with soy protein was prepared for concentrations between 10 µg/mL and 1500 µg/mL. Solubility Index was calculated as follows:

$$NSI\% = (Prot_S/Prot_T) \times 100$$

where $Prot_S$ is the concentration of soy protein in the supernatant and $Prot_T$ is the concentration of soy protein in the solution before centrifugation.

Tablets Preparation

Soy protein tablets were formed using a Carver press (Autopellet laboratory press, Carver Incorporation, Wabash, Ind.). Each tablet was 400 mg±10 mg weight and 13 mm in diameter. Tablet formation was led using a compression force of 9000 lbs for 1.5 min. In the case of riboflavin and rifampicin loaded tablets for dissolution experiment, drug content represented 10% of the tablet mass.

Erosion and Swelling Experiments

Tablet spontaneous erosion evaluation was carried out using a USP I apparatus (Distek Inc., North Brunswick, N.J.) by measuring the quantity of protein released by tablets as a function of time. Tablets were immersed in 750 mL of dissolution media and absorbance at 280 nm was measured until such time that protein loss remained under 10% of the tablet initial weight. Absorbance was converted in protein concentration in mg and scaled as a function of time. Dissolution media consisted in 60 mM NaH$_2$PO$_4$ buffer (pH 7.5) and a 60 mM HCl solution (pH 1.2). Protein loss was calculated as follows:

$$Protein\ Loss = (Prot_t/Prot_T) \times 100$$

where $Prot_t$ is the quantity of protein released at a time t and $Prot_T$ is the tablet initial mass.

Tablet dynamic swelling was measured as follows. Tablets were immersed in 25 mL of swelling medium and tablets were briefly blotted then weighed at several time intervals. Tablet swelling ratio ($S_r$) was calculated from the difference in mass before and after immersion. Swelling was measured until such time that protein loss remained under 10% of the tablet initial mass. Two media were used: a 60 mM NaH$_2$PO$_4$ buffer (pH 7.5) and a 60 mM HCl solution (pH 1.2). The swelling ratio of the tablet ($S_r\%$) was calculated as follows:

$$S_r = [(W_{AS} - W_{BS})/(W_{BS})] \times 100$$

where $W_{BS}$ is the tablet weight before swelling and $W_{AS}$ is the tablet weight after swelling. All measurements were performed in triplicate.

Dissolution Experiments

Dissolution studies were performed according to Pharmacopoeia official methods (2004). Basket apparatus I was used with a temperature circulator/controller both from Distek Inc. (North Brunswick, N.J.). Agitator speed was set at 90 rpm and the temperature was maintained at 37±0.5° C. Release measurements were made using an automatic sampling system connected to a spectrophotometer (Agilent Technologies, Germany). The dissolution volume was maintained constant at 900 mL.

The simulated gastric fluid consisted of 2 g of sodium chloride, 7 mL of 37% hydrochloric acid, and 1000 mL of HPLC grade water. The final pH was 1.2. Dissolutions were carried out with and without pepsin (3.2 g, 924 units/mg of protein) to evaluate release in the presence and the absence of enzyme. Dissolution of the different gels was followed for 6 h.

The simulated intestinal fluid consisted of 6.8 g of monobasic potassium phosphate dissolved in 250 mL of HPLC grade water and added to 190 mL of 0.2N sodium hydroxide and 400 mL of HPLC grade water. Dissolution was carried out with and without pancreatin (10 g, activity equivalent to USP specification) added to this mixture. The pH was adjusted to 7.5±0.1 using 0.2N sodium hydroxide, and the final volume was then brought to 1000 mL with double distilled water. Dissolution of the different gels was followed for 6 h.

Two model molecules were used during dissolution experiments: riboflavin, highly soluble vitamin and rifampicin, an antibiotic of low solubility.

The amount of degradation of the compressed tablets is determined during 4 h by measuring the absorbance of the dissolution media at 280 nm. The dissolution volume is fixed at 750 mL. A standard IPS curve, in which concentrations extend from 40 mg/L to 2000 mg/L, is produced.

The rate of degradation is determined by the equation given by Sriamornsak et al. (2007):

$$E = \frac{Q_t}{P_0} \times 100$$

where E is the degradation rate, $Q_t$ is the quantity of proteins as measured at time t, and $P_0$ is the initial weight of the compressed tablet.

Degradation of three compressed tablets was measured for each type of compressed tablet.

Dissolution Data Analysis

In order to study the transport mechanism of riboflavin and rifampicin from the different loaded hydrogels, the data were modeled by the Ritger-Peppas equation at $M_t/M_\infty < 0.6$ (Ritger and Peppas 1987):

$$M_t/M_\infty = k \cdot t^n$$

where $M_t/M_\infty$ is the fractional drug release, k is a kinetic constant and n is the diffusional exponent that can be related to the drug transport mechanism. For a cylinders, when n=0.45, the drug release mechanism is Fickian diffusion. When n=0.89, Case II transport occurs (indicating a swelling-controlled drug release). When the value of n is between 0.45 and 0.89, anomalous transport is observed (indicating the superposition of both phenomena) (Siepmann and Peppas 2001). $M_\infty$ is the amount of drug released at equilibrium. Each experiment was performed in three cells.

Study of the release of the active agents from the charged compressed tablets is carried out during 6 h by measuring the absorbance of the dissolution media at 445 nm for riboflavin and 473 nm for rifampicin. The dissolution volume was 900 mL. Standard curves were produced for each of the active molecules. The concentrations of the standard curve for riboflavin range from 3.75 mg/L to 60 mg/L while those of the standard curve for rifampicin vary between 4 mg/L and 100 mg/L.

The release kinetics may be characterized by determining the coefficient n in the equation given by Siepmann and Peppas (2001):

$$\frac{M_t}{M_\infty} = kt^n$$

where $M_t$ is the quantity of active agent released at time t
$M_\infty$ is the maximum quantity of active agent that can be released
k and n are coefficients which are dependent on the nature of the system under study and the interactions between this system and the active molecule.

Determination of the coefficient n is carried out by linearization of the above mentioned equation:

$$\log\left(\frac{M_t}{M_\infty}\right) = n \log t + \log k$$

The value of n then corresponds to the slope of the straight line obtained. Depending on the value of the coefficient n, it is possible to characterize the release kinetics of the active agent.

Statistical Analysis

Statistical analyses were performed using JMP software (version 4, SAS Institute, Cary, N.C.). Log-log plots slopes (n) in the Ritger-Peppas equation were calculated using a linear regression.

Example 2

Results/Discussion

Succinylation is a chemical modification which should not cause problems when ingested in the form of compressed tablets because succinic anhydride, which could eventually be left after the reaction, is converted into succinate which is a component of the oxidative metabolism.

Trials with Various Molar Ratios

In order to obtain solutions of succinylated soy proteins with exact yields, we prepared solutions of succinylated soy proteins with various molar ratios of succinic anhydride:amine groups.

To determine the extent of blocking of the amine groups by succinylation, the OPA method was preferred instead of dosing with ninhydrine since the latter method appeared to be less efficient (Panasiuk et al., 1998). Another method could have been considered: dosing with 2,4,6-trinitrobenzene-sulfonic acid (TNBS). This method performs similarly as the OPA method (Panasiuk et al., 1998).

Figure 2:
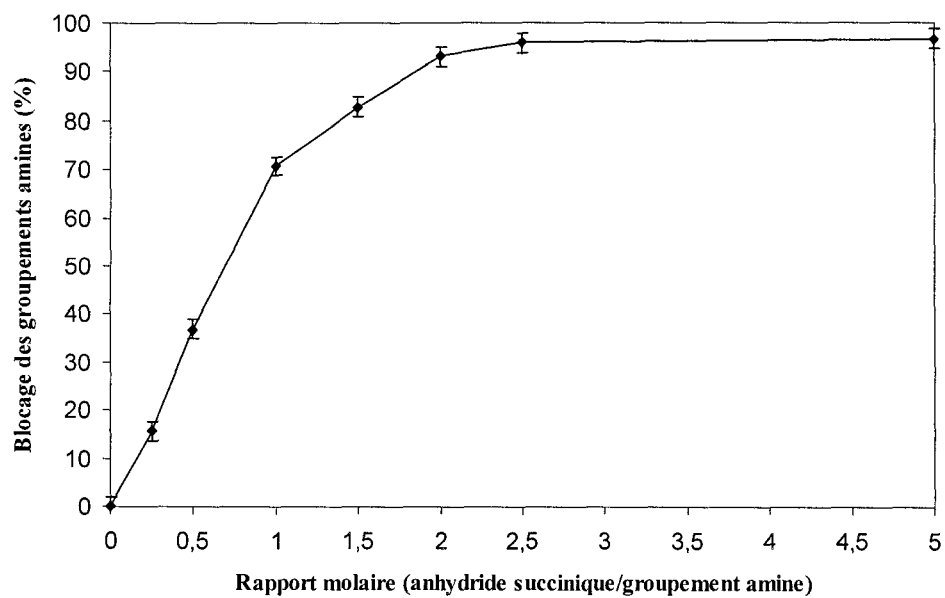
FIG. 2: Extent of succinylation in function of various molar ratios of succinic acid.

FIG. 2 shows the extent of blocking of the amine groups on the basis of succinic anhydride:amine group molar ratio. On this curve, a first linear part is noted, and a plateau appears when a molar ratio of 2.5 is reached. This experiment allows us to see that the succinylation reaction is not complete since, for a molar ratio of 1, blocking is only 70%. To obtain nearly complete blocking, it is necessary to achieve a molar ratio of 2.5 of anhydride/amine group. In order to determine the molar ratio that is required for a succinylation rate of 50%, it is possible to use the linear part of the curve; this ratio amounts to 0.7. Therefore, it is possible to prepare solutions which are 50% and 100% succinylated by providing anhydride over amine groups molar ratios of 0.7 and 2.5 respectively.

Succinylation Impact on Soy Proteins Secondary Structure

Figure 3:
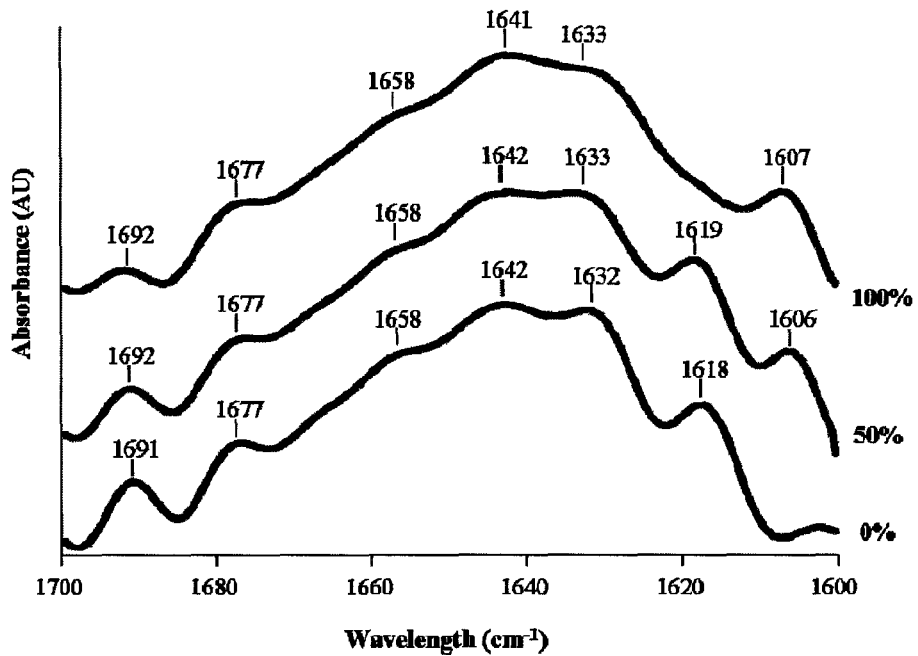
FIG. 3: Deconvoluted FTIR spectra of soy proteins as a function of succinylation degree.

FIG. 3 presents the de-convoluted spectra in the amide I' region for a native soy protein solution and for 50% and a 100% succinylated soy protein solution. The unmodified protein spectrum is composed of eight bands located at 1602, 1618, 1632, 1642, 1658, 1677 and 1691 $cm^{-1}$. Components located at 1632, and 1677 $cm^{-1}$ are attributed to β-sheets (Arrondo et al. 1993, Lefèvre and Subirade 2000). Soy protein secondary structure in fact consists of about 60% β-sheet (Hwang and Damodaran 1996). The band located at 1642 $cm^{-1}$ was attributed to unordered structure (Arrondo et al. 1993, Meng et al. 2001, Ellepola et al. 2005). The 1658 $cm^{-1}$ vibration has been attributed to the presence of small amounts of α-helix in soy globulins (Arrondo et al. 1993, Meng et al. 2001, Ellepola et al. 2005). The component located at 1618 $cm^{-1}$ indicated the presence of intermolecular β-sheets, suggesting the presence of protein aggregates (Lefèvre and Subirade 2000, Meng et al. 2001, Ellepola et al. 2005), while the 1691 $cm^{-1}$ vibrations were attributed to the presence of turns (Lefèvre and Subirade 2000, Meng et al. 2001). The minor component located at 1602 $cm^{-1}$ was thought to be due to amino acid residue vibration.

The effect of succinylation on soy globulin secondary structure appears mainly as a disappearance of the 1618 $cm^{-1}$ component, which could be correlated with a decrease of aggregation between proteins (Jackson and Mantsch 1992). Indeed, succinylation would lead to a protein unfolding and a dissociation of aggregated proteins or proteins subunits (El-Adawy 2000). Such an unfolding was already noted by Subirade et al. 1992 and Schwenke et al., 1993. Moreover, grafting carboxylic groups on proteins was already shown to lead to the same result. Indeed, a decrease of aggregation has already been observed in the case of soy proteins modification with EDTAD (Ethylene Diamine TetraAcetic Dianhydride) (Hwang and Damodaran 1996). Finally, succinylation would lead to a disappearance of the 1602 $cm^{-1}$ band and the appearance of a component located at 1607 $cm^{-1}$. This band is thought to be related to the amino side chain vibration (Lefèvre and Subirade 2000). This increase would result from protein unfolding that would increase the exposure of amino acid side chain and thus an increase of their vibration.

Succinylation Impact on Soy Proteins Zeta Potential

Figure 4:
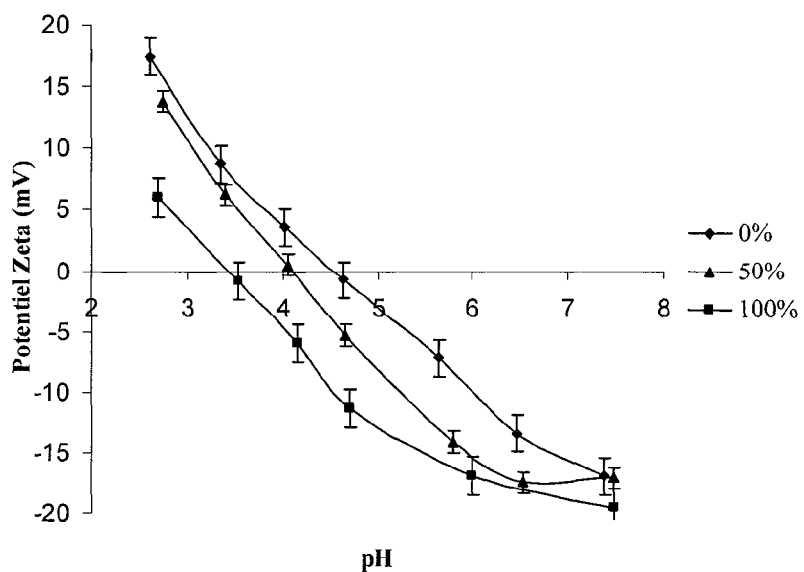
FIG. 4: Soy protein zeta potential value as a function of pH and succinylation rate.

The impact of succinylation on proteins charge was evaluated using zeta potential measurements. FIG. 4 illustrates the dependence of succinylated soy proteins and unmodified proteins zeta potential on the pH media. Protein zeta potential is equal to zero at protein isoelectric point (pI), is positive below proteins pI (the protein is globally positively charged) and is negative above soy proteins pI (the protein is globally negatively charged). It appears that succinylation induces an increase of proteins' zeta potential value for pH above the soy protein's pI while succinylation leads to a decrease of the zeta potential for pH below the protein isoelectric point. Indeed, succinylation introduces anionic succinate residues covalently linked to the s-amino groups of lysine residues. The resulting change from positively to negative charges leads to the observed modification in protein zeta potential. Moreover, because of its impact on protein surface charge, succinylation induces a decrease of the soy protein isoelectric point from about 4.5 to 3.5.

Impact of Succinylation on Soy Proteins Solubility

Figure 5:
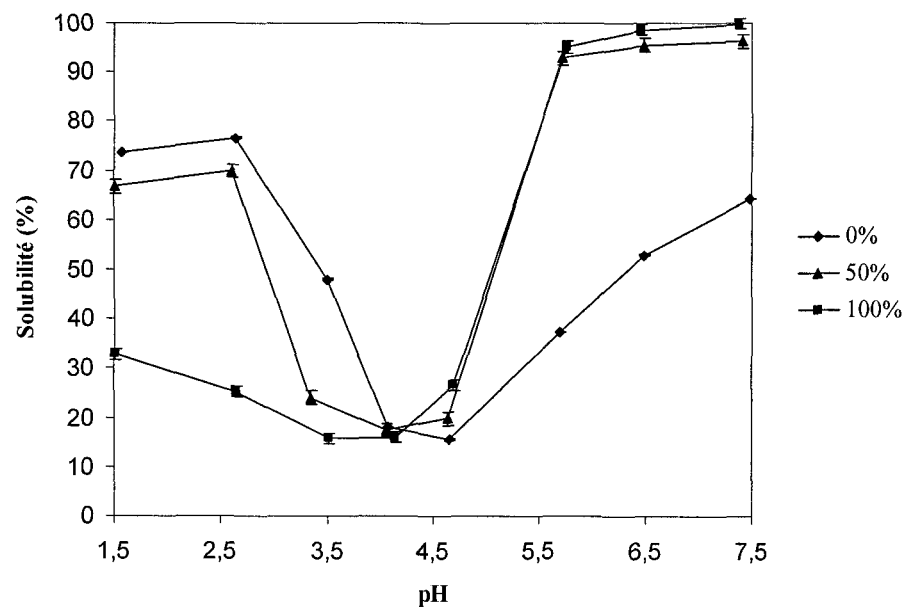
FIG. 5: Soy protein nitrogen solubility index as a function of pH and modification degree.

The impact of succinylation on soy proteins solubility is presented in FIG. 5. It appears that succinylation leads to an increase of the nitrogen solubility index at pH above protein isoelectric point and a decrease of its solubility at pH below soy proteins pI. These modifications of soy proteins solubility are directly connected to the zeta potential modifications previously observed. In succinylated proteins, amino groups are replaced by carboxylic groups, consequently at acidic pH, amino group content is reduced and proteins carboxylic groups are protonated, leading to a decrease in protein solubility. On the contrary, at pH above the soy protein pI, the higher content in ionized carboxylic groups for modified soy proteins leads to an increase in their solubility. These changes in soy proteins solubility have already been observed by other authors in the case of protein succinylation (Achouri et al. 1998, El-Adawy, 2000).

Modification Rate Influence on Tablets Erosion and Swelling

Tablets spontaneous erosion as well as tablets swelling ratio ($S_r$) and its dependence on soy proteins succinylation rate and pH have been studied. Swelling consists in the spontaneous water uptake of the matrix as a function of time. However, depending on the physical chemical conditions (pH), it appears that solvent uptake can lead to an erosion of the tablets leading to a protein loss. Consequently, in that case, tablets dissolve rather than swell and no swelling can be measured. Thus, in order to take into account this phenomenon and study tablets swelling, tablets erosion was firstly measured. Swelling was considered as still significant while protein loss remain below 10% of the initial tablet mass. Results obtained from these experiments at pH 1.2 and pH 7.5 are respectively presented in FIGS. 6 and 7.

Regardless of the protein succinylation rate, the tablets protein loss ratio and the tablets swelling ratio were shown to be dependent on swelling medium pH. Both were shown to be more important at pH 7.5 than at pH 1.2.

Figure 6A:
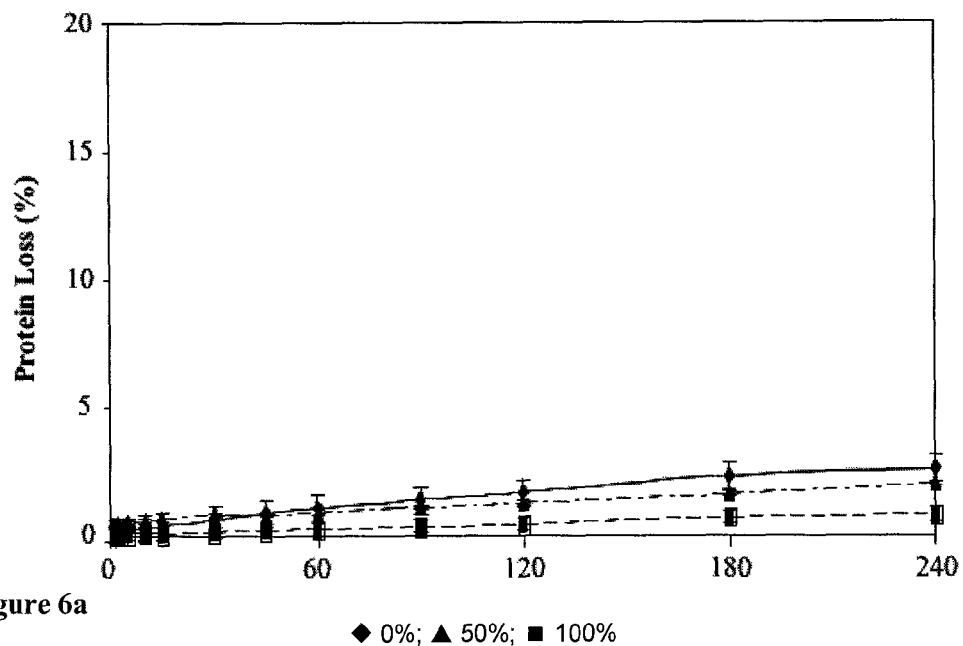
FIG. 6: Soy protein tablets spontaneous erosion rate (a) and swelling rate (b) as a function of time and protein succinylation degree in simulated gastric fluid in the absence of pepsin.
Figure 6B:
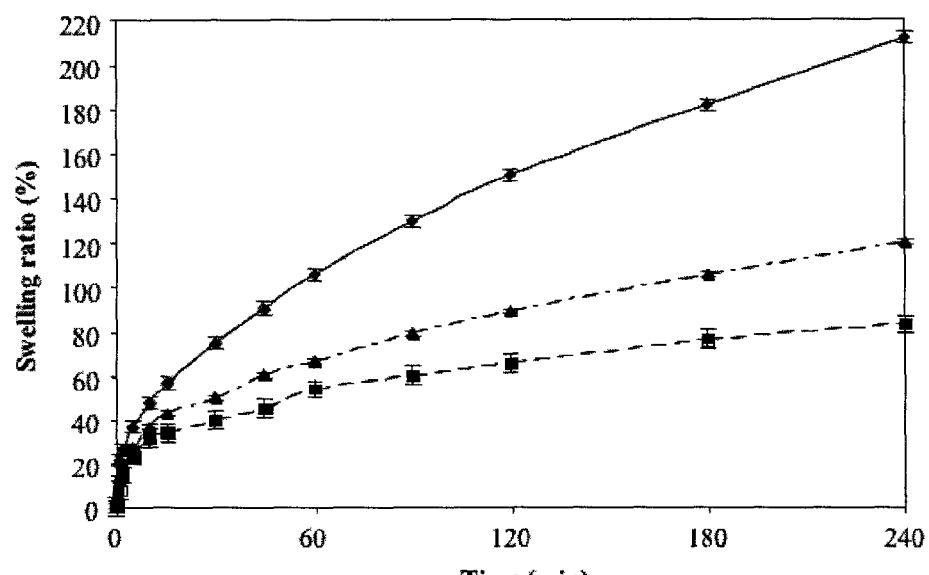

It appears that at pH 1.2, protein loss rate was shown to be very low for all tablets (FIG. 6a). Succinylation only induces a slight decrease in tablets erosion rate. However, tablets swelling rate was particularly affected, an increase of proteins modification leading to an important decrease of tablets swelling rate (FIG. 6b).

Figure 7A:
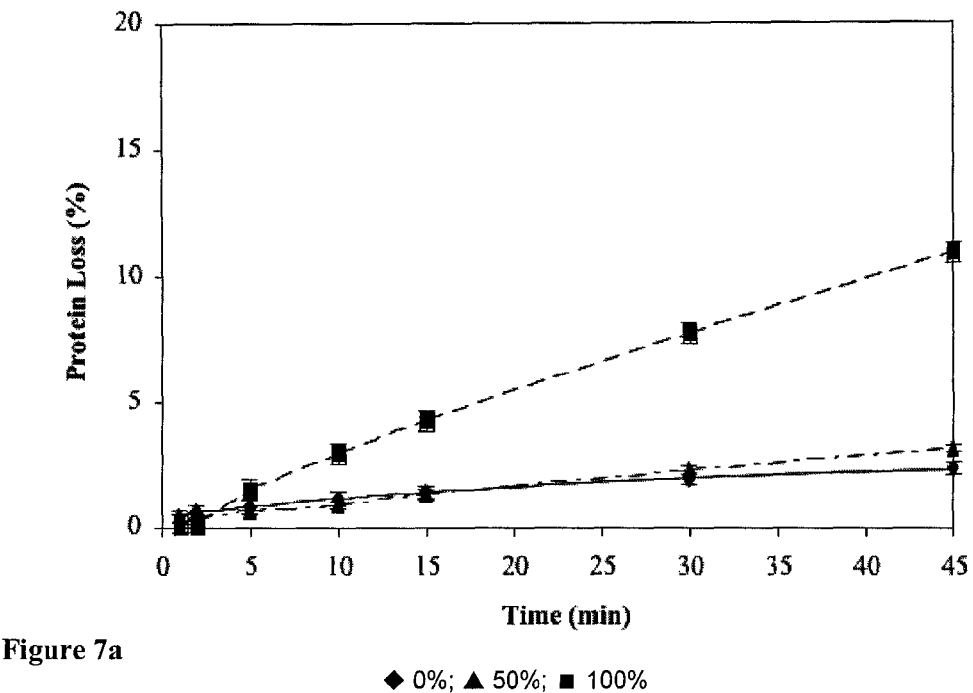
FIG. 7: Soy protein tablets spontaneous erosion rate (a) and swelling rate (b) as a function of time and protein succinylation degree in simulated intestinal fluid in the absence of pancreatin.
Figure 7B:
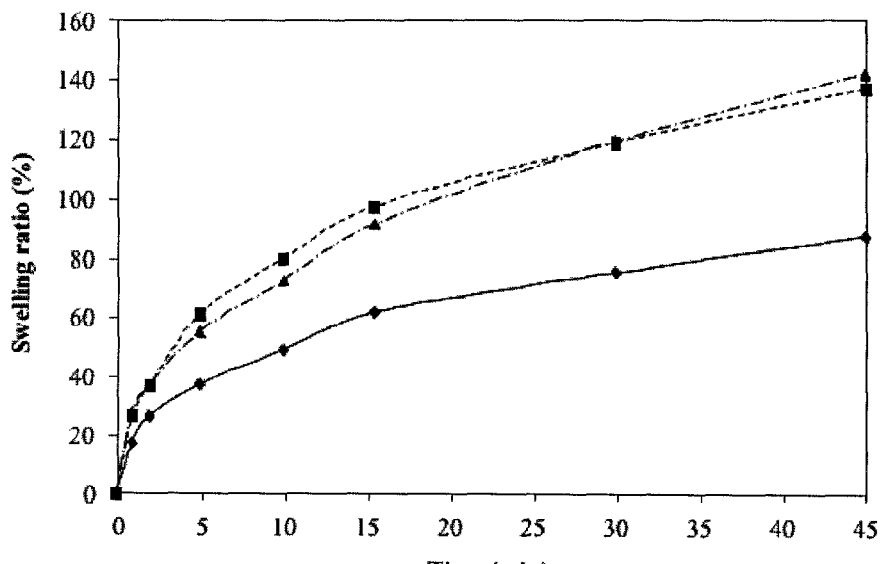

At pH 7.5, the inverse results were observed. It appears that an increase of protein succinylation rate would lead to an important increase of tablets erosion and tablets swelling (FIGS. 7a and 7b).

Kavanagh and Ross-Murphy (1998) reported that when a biopolymer network is in contact with an aqueous solution or a biological fluid, the network starts to swell due to the thermodynamic compatibility of the polymer chains and water (to its good solubility). The retracting forces induced by the network cross-links (considered absent in the present case) counter-balance the swelling force. However, when ionic moieties are present in the polymer, as in the case of protein tablets, the thermodynamic treatment is more complex and another contribution to the equilibrium must be added. This ionic contribution will depend on the charge of the polymer, so pH media and its ionic forces will play an important role in the phenomenon.

In the present work, succinylation was shown to decrease protein ionic charge/proteins solubility at pH 1.2 and increase protein ionic charge/proteins solubility at pH 7.5, consequently it seems that ionic repulsions between proteins as well as protein affinity to solvent are decreased at pH 1.2 and increased at pH 7.5, leading to a decrease of tablets erosion/swelling at acidic pH and an increase of tablets protein loss/swelling at neutral pH. It should be noted that such an increase in solvent uptake at neutral pH has already been shown in the case of soy protein modification by EDTAD (that consists in grafting carboxylic moieties on amino groups) in order to form hydrogels with modifiable release properties (Hwang and Damodaran, 1996).

Consequently, it appears that tablets erosion and tablets swelling are strongly dependent on pH media and the extent of protein succinylation.

Impact of Modification on Drug Release Properties in Gastro Intestinal Fluids Without Enzymes In order to get a better understanding of the dependence of soy proteins modification on tablets release mechanisms, in vitro release studies have been carried out with riboflavin and rifampicin loaded tablets formed with unmodified proteins, 50% succinylated proteins and 100% succinylated proteins. Several physico-chemical conditions were studied: Gastric Simulated Fluid (GSF) and Intestinal Simulated Fluid (ISF) in the absence and the presence of enzymes.

Figure 8A:
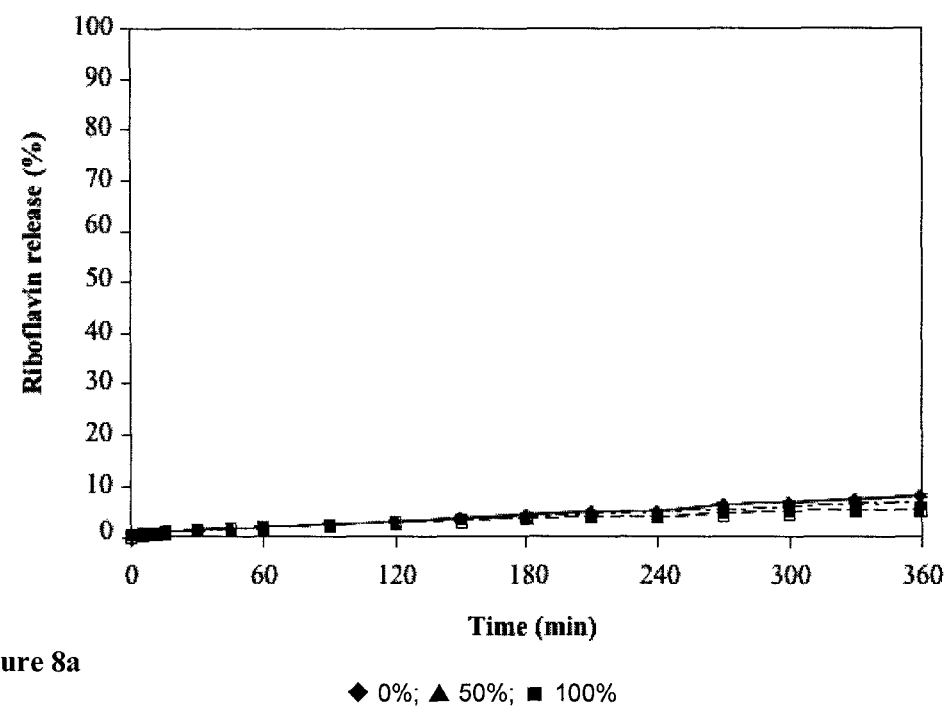
FIG. 8: Riboflavin release profiles in (a) SGF in the absence of pepsin, (b) in SIF in absence of pancreatin, and (c) in SGF in presence of pepsin.
Figure 9A:
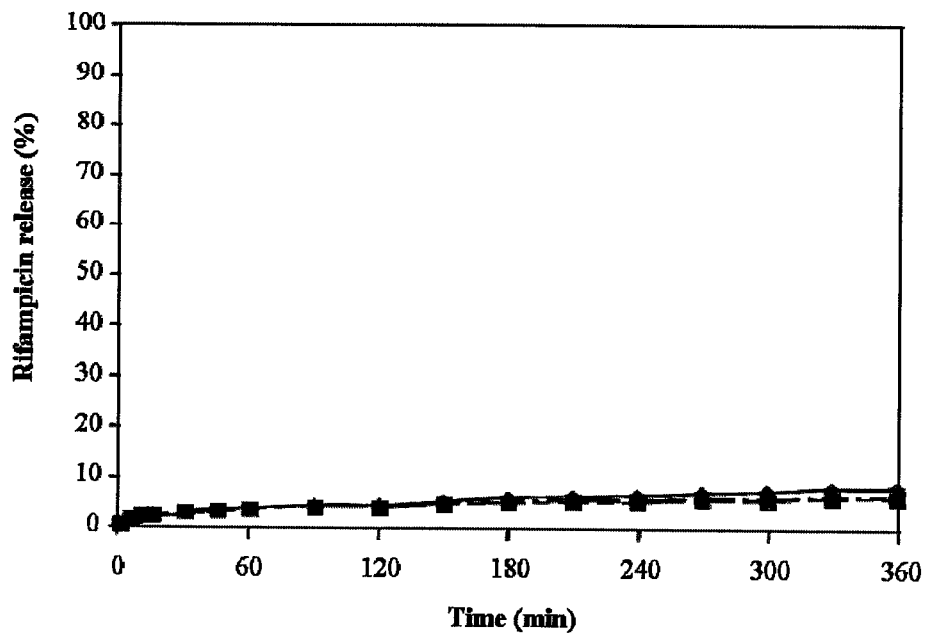
FIG. 9: Rifampicin release profiles in (a) SGF in the absence of pepsin, (b) in SIF in absence of pancreatin, and (c) in SGF in presence of pepsin.

FIGS. 8a and 9a illustrate the release profiles obtained from the selected tablets in GSF without enzymes for riboflavin and rifampicin loaded tablets respectively. In gastric simulated conditions, it seems that tablets release properties are influenced very little by the extent of protein modification or drug type. It appears that drugs release was diminished very little while soy protein modification was increased. This result is a bit surprising if succinylation impact on tablets swelling at pH 1.2 is considered. Indeed, succinylation was shown to strongly influence tablet swelling in gastric media. This result could indicate that swelling phenomena influences only slightly drug release at gastric pH for the selected tablets.

Figure 8B:
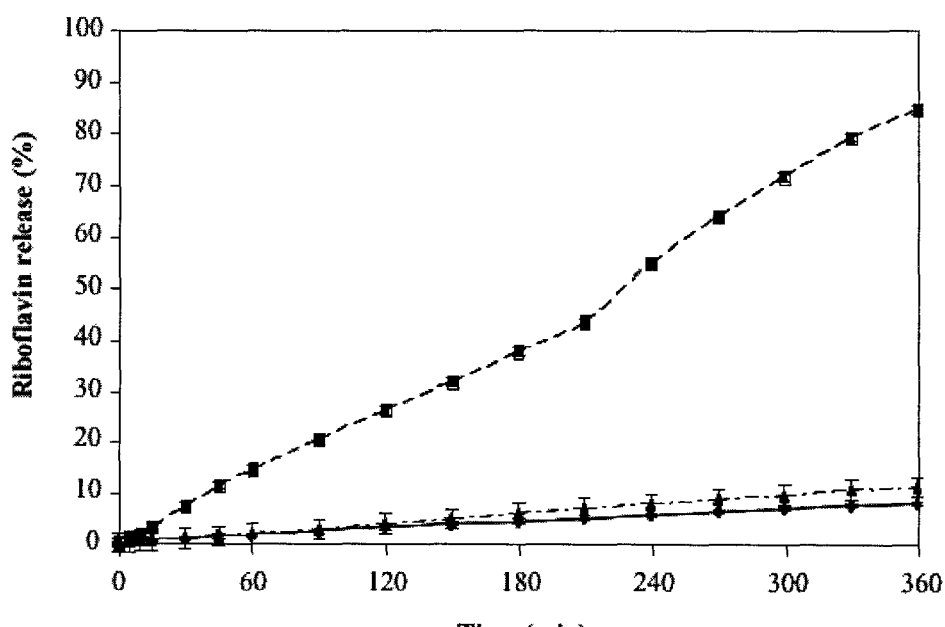
Figure 9B:
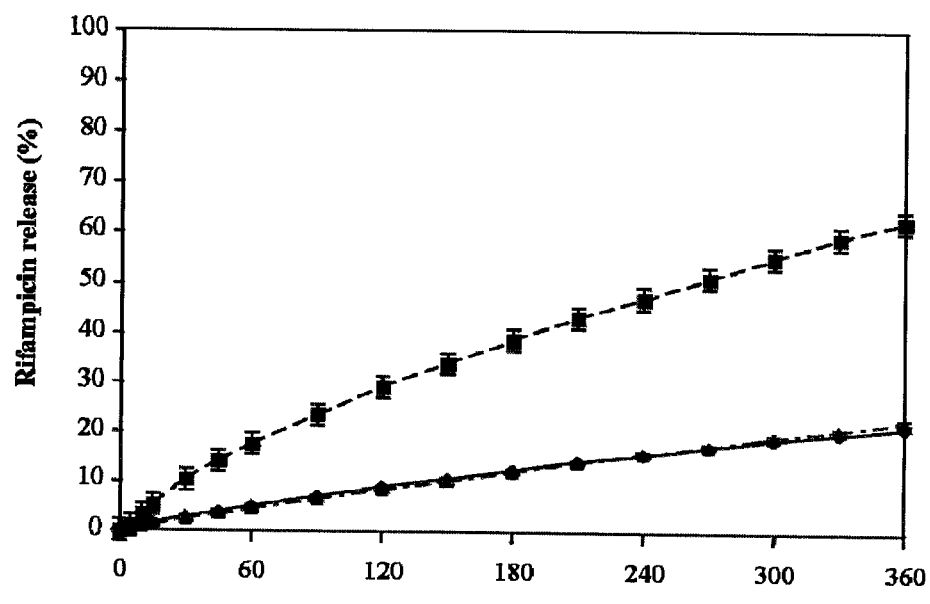

On the contrary, in intestinal simulated conditions without enzymes, regardless of the drug, while a 50% protein succinylation was shown to only slightly increase drug release, 100% protein modification was shown to largely increase drug release (FIGS. 8b and 9b). It has been shown previously that tablets erosion was strongly influenced by protein modification at pH 7.5. Consequently, this phenomenon is thought to influence in an important manner drug release at intestinal pH.

Finally, in order to study drug release mechanisms from the different selected tablets, the data were modeled by the Ritger-Peppas equation at $M_t/M_\infty < 0.6$ (Ritger and Peppas, 1987), n exponent were calculated for each tablet and are reported in Tables 1a and 1b for respectively riboflavin and rifampicin loaded matrix. All tablets presented a linear relationship with high correlation in the log-log plot.

It appears that at pH 1.2, riboflavin loaded tablets (Table 1a) presented a n coefficient between 0.45 and 0.89 that is consistent with an anomalous transport where diffusion and relaxation (swelling) phenomena are both responsible of drug release. On the contrary, rifampicin loaded tablets (Table 1b) showed a n coefficient near 0.45, indicating a release mechanism dominated by fickian diffusion.

TABLE 1a n coefficient for riboflavin-loaded modified soy protein tablets

| | Succinylation rate | | |
|---|---|---|---|
| | 0% | 50% | 100% |
| pH 1.2 | 0.724 ± 0.036 | 0.809 ± 0.027 | 0.689 ± 0.023 |
| pH 7.5 | 0.839 ± 0.059 | 0.895 ± 0.107 | 1.042 ± 0.059 |

TABLE 1b n coefficient for rifampicin-loaded modified soy protein tablets

| | Succinylation rate | | |
|---|---|---|---|
| | 0% | 50% | 100% |
| pH 1.2 | 0.567 ± 0.073 | 0.4210 ± 0.051 | 0.407 ± 0.071 |
| pH 7.5 | 0.837 ± 0.047 | 0.995 ± 0.030 | 0.961 ± 0.016 |

At pH 7.5, regardless of the loaded molecule, unmodified protein tablets showed n coefficient near 0.89, indicating a swelling-dominated release mechanism. However, in the case of modified soy protein matrix, it seems that n coefficients are increased and tend to be above 0.89, indicating a super case II transport. This kind of release would describe a transport in which the diffusion coefficient depends on both the concentration and time and in which the rate of solvent uptake into the polymer is largely determined by the rate of swelling and relaxation of the polymer chains (Sezer and Akbuga, 1995). In the present case, this behavior is thought to be connected to the important erosion of succinylated tablets at pH 7.5. Indeed, because of their high solubility at pH 7.5 (FIG. 5), tablets probably tend to dissolve in intestinal simulated conditions. Moreover, because of the increase of the ionic repulsions between proteins while succinylation is increased, riboflavin and rifampicin release is accelerated. This hypothesis would be confirmed by visual observation: indeed, during release, gels size was reduced fast and continuously. We can note that an increase of tablet erosion while excipient solubility is increased was shown by author authors in the case of cationic gum guar/poly acrylic acid tablets (Huang et al., 2007).

Release studies of tablets were also led in GSF and ISF in the presence of enzymes in order to understand tablets release behavior in the gastro intestinal tract.

Figure 8C:
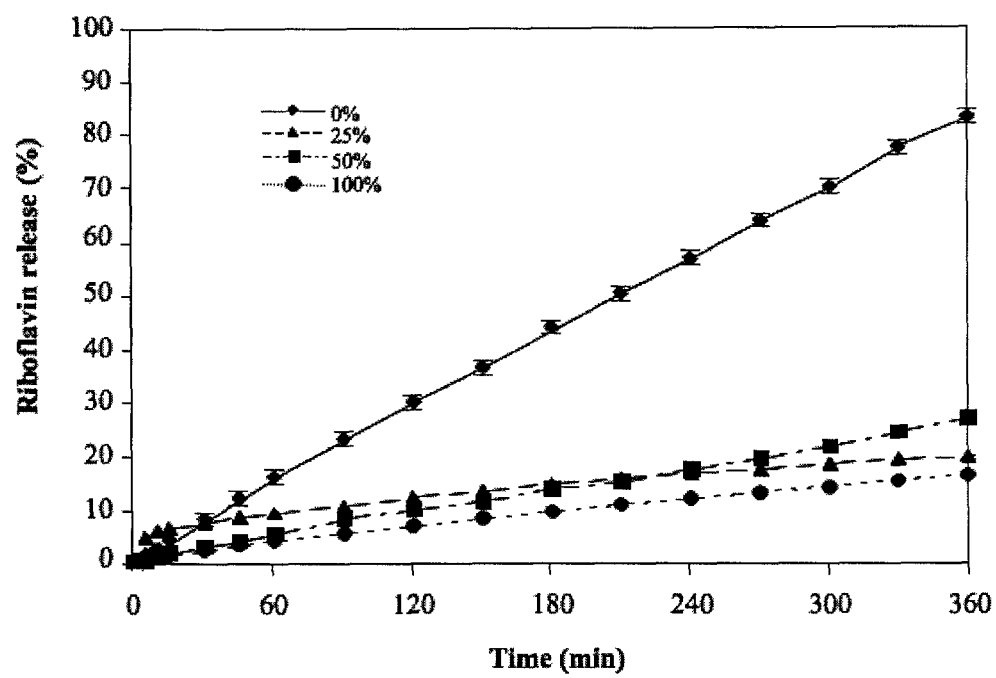
Figure 9C:
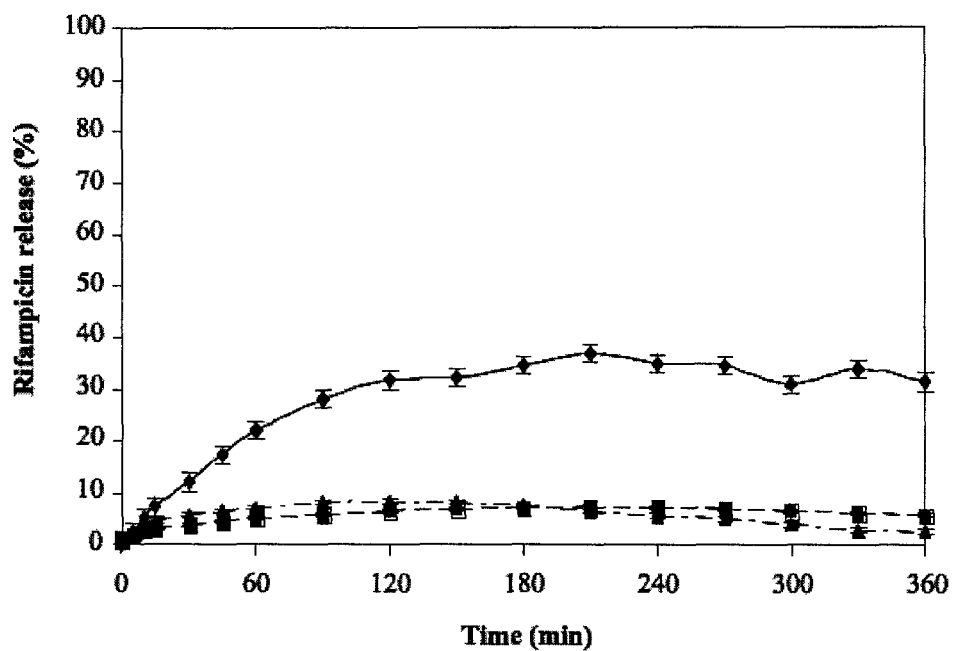

Riboflavin and rifampicin release profiles in gastric simulated conditions are presented in respectively FIGS. 8c and 9c. While few differences were shown in gastric medium without enzymes, it seems that in the presence of pepsin, riboflavin and rifampicin release are strongly influenced by protein succinylation. Modified protein tablets showed only very little release (less than 15% after 6 hours) indicating that succinylated proteins tablets lead to an important decrease of riboflavin release in gastric medium. However, we can note here that riboflavin release seemed to be more important than rifampicin release, probably because of its higher solubility. Consequently, assuming that the average gastric residence time is between 30 min (empty stomach) and about 4 h (ingestion of a nutritive meal) (Ewe et al., 1991) it seems that succinylated proteins constitute an interesting excipient in order to pass through stomach conditions without releasing drug.

Figure 10:
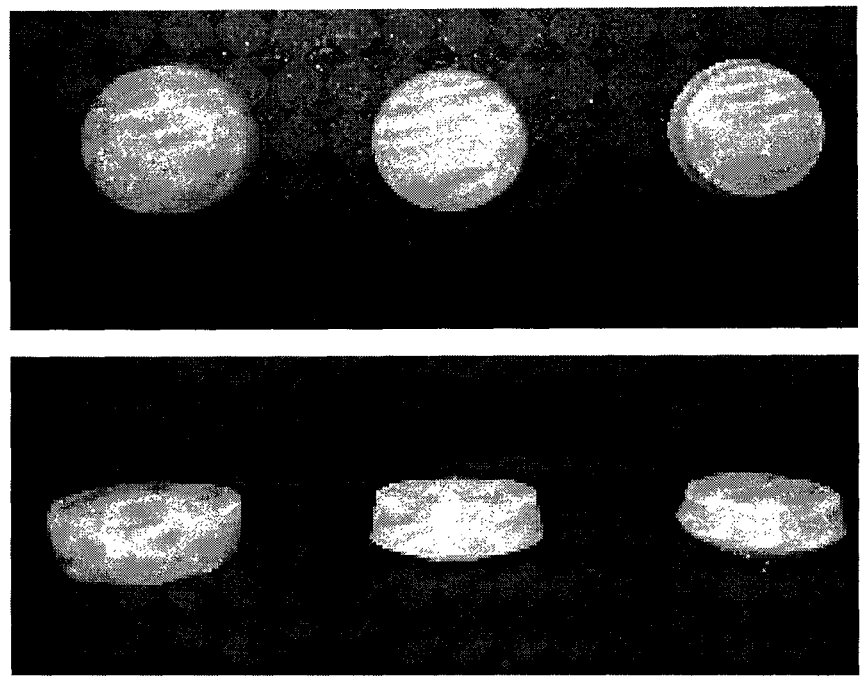
FIG. 10: Tablets photographs after 4 h immersed in simulated gastric fluid in absence of pepsin.

It should be noted that Achouri and Zhang (2000) have shown that succinylation, because of its impact on protein unfolding led to an increase of its enzymatic digestibility. Consequently, our results are unexpected. These results are thought to be connected to the potential impact of succinylation on proteins interactions when compressed. Without wishing to be bound by this theory, according to the DLVO theory, when ionic repulsions between proteins are diminished, short distances forces such as van der waals attractions and hydrophobic effect are favored and can potentially lead to the formation of an impermeable erosion barrier at the surface of the tablet. This hypothesis needs to be further investigated; however, it tends to be confirmed by visual observation. FIG. 10 illustrates pictures taken from tablets after a 4 h immersion in gastric media. It appears that while proteins succinylation is increased, a solid layer appears on the surface of the tablet that is thought to decrease tablet biodegradation.

Figure 11:
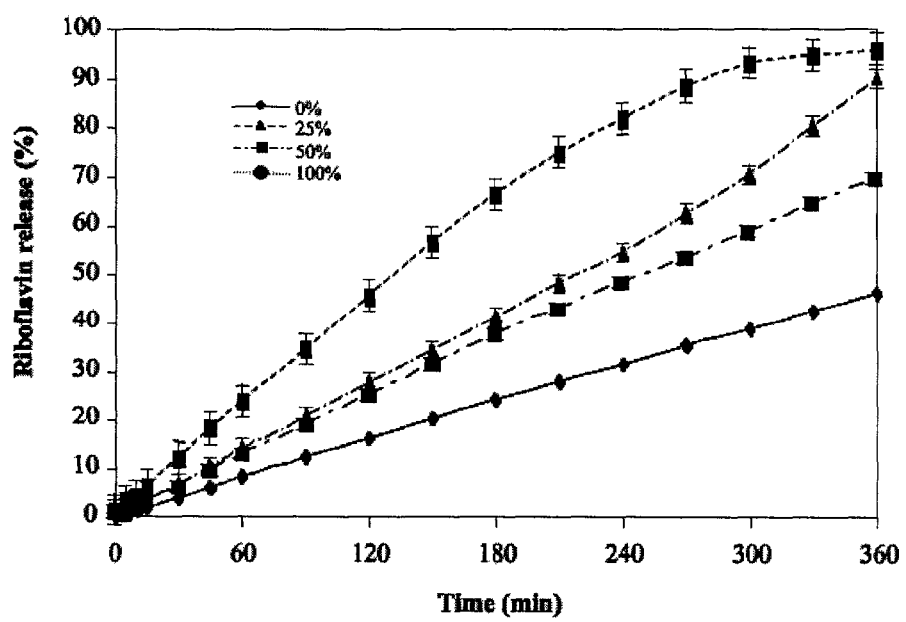
FIG. 11: Riboflavin release profile in SIF in presence of pancreatin.
Figure 13:
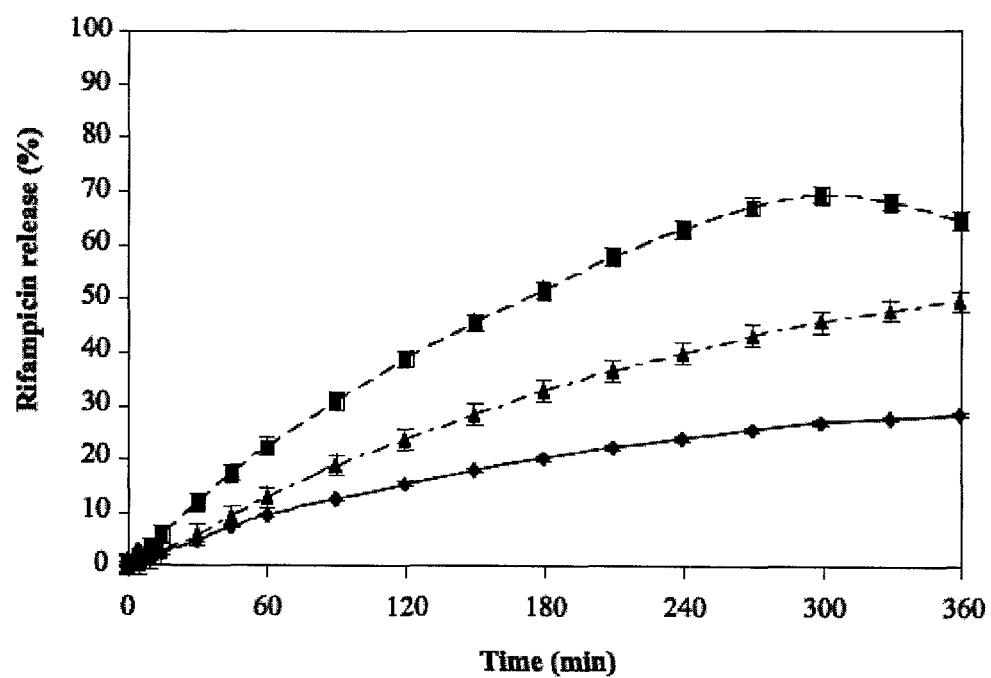
FIG. 13: Rifampicin release profiles in (a) SIF in presence of pancreatin.

Finally, in order to study succinylated proteins tablets release properties in the intestine, release studies were led in ISF, in the presence of pancreatin. FIGS. 11 and 13 illustrate respectively release profiles obtained from riboflavin and rifampicin loaded matrix.

It seems that, as previously observed in the case of dissolution experiments in ISF without enzymes, release is strongly favored by protein succinylation. Pancreatin presence would only accelerate the previous observed release profiles. Also, it is important to mention that release profiles tend to be linear, indicating a zero order release kinetic. This result is more pronounced in riboflavin release case. The pharmaceutical dosage forms following this profile releases the same amount of drug by unit of time and it is the ideal method of drug release in order to achieve a pharmacological prolonged action (Costa and Lobo, 2001).

Influence of Different Types of Protein

Figure 12A:
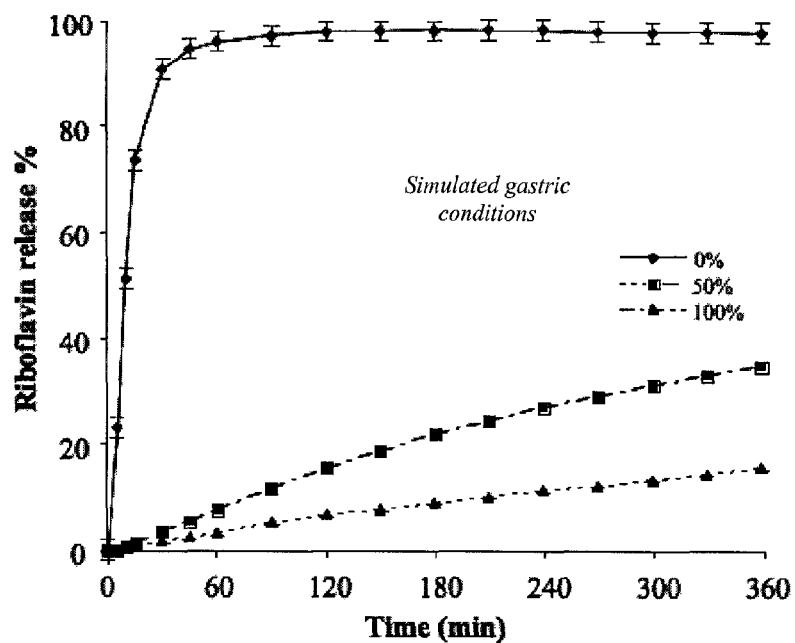
FIG. 12: Riboflavin release profiles when mixed with succinylated β-lactoglobulin in (a) SGF in presence of pepsin; and (b) SIF in presence of pancreatin.
Figure 12B:
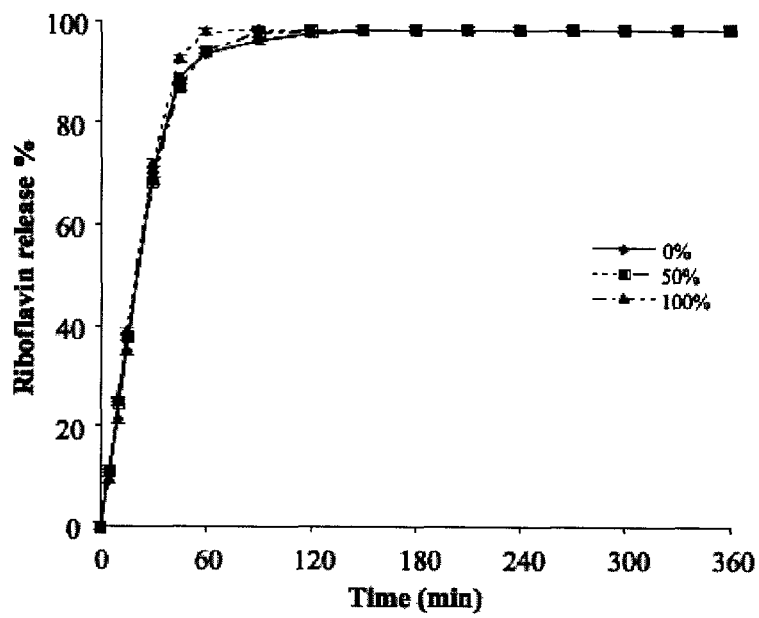

The impact of different types of proteinic material was assessed on release properties of drug-excipient systems using tablets made up from succinylated β-lactoglobulin. In vitro dissolution experiments were carried out with vitamin B2 as a model. Experiments in the presence of digestive enzymes (FIGS. 12a and 12b) showed that release profiles are strongly influenced by the type of protein used in the system, however the impact of the succinylation ratio is maintained inasmuch as the release profile in gastric media is the same soy proteins.

It is important to note here that, although soy proteins achieved a zero order kinetic in simulated intestinal phase leading to a delayed release of the active ingredient, β-lactoglobulin would in contrast lead to a kinetic of order 1 in simulated intestinal phase. This result can be explained by the very high solubility of β-lactoglobulin at pH 7.5, leading to a rapid dissolution of tablets. This results suggest the importance of choosing the right proteinic excipient for each type of active ingredient. In certain instances, a zero order kinetic is desired, whereas in other instances a kinetic of order 1 is acceptable or desirable inasmuch as gastro resistance is achieved.

Other proteins that may be used as excipient in the present invention include, for example: globulins, albumins, caseins, glutelins, prolamines (particularly poor in lysine and mostly soluble in ethanol), histones and protamines (with generally high pI), fibrous proteins (such as collagen) or heteroproteins or caseinates (sodium or calcium), lipoproteins, glycoproteins, etc. Of particular interests are food proteins which are known to be innocuous, well tolerated and cheap (often representing wasted material from food production processes).

Example 3

Gastric Protection of a Probiotic

One aspect of this experiment was aimed at determining bacterial survival following gastric passage of 30, 60 or 120 minutes, and another aspect was geared towards determining the impact of percent succinylation of the protein (β-lactoglobulin at 0, 50 et 100%) on tablet gastro-resistance. 400 mg tablets containing 10% of lyophilized bacteria and formed at 67 MPa for 30 sec were used.

Formed tablets were incubated in 400 mL of SGF to which about 1.28 g of pepsin was added. The incubation was carried out under constant stirring (about 160 rpm), at 37° C. during 30, 60 or 120 minutes. The tablet was then transferred in 25 mL of SIF (without enzyme) and then was vortexed until complete dissolution of the tablet and/or suspension of the solid. This suspension was then diluted in series (by factor 10) and then 1 mL of chosen dilution was seeded in duplicate. Sedding was carried out in MRS medium+0.05% cysteinHCl. Petri dished were incubated at 37° C. for 48 h in an anaerobic container and remaining CFU were then counted.

Figure 14:
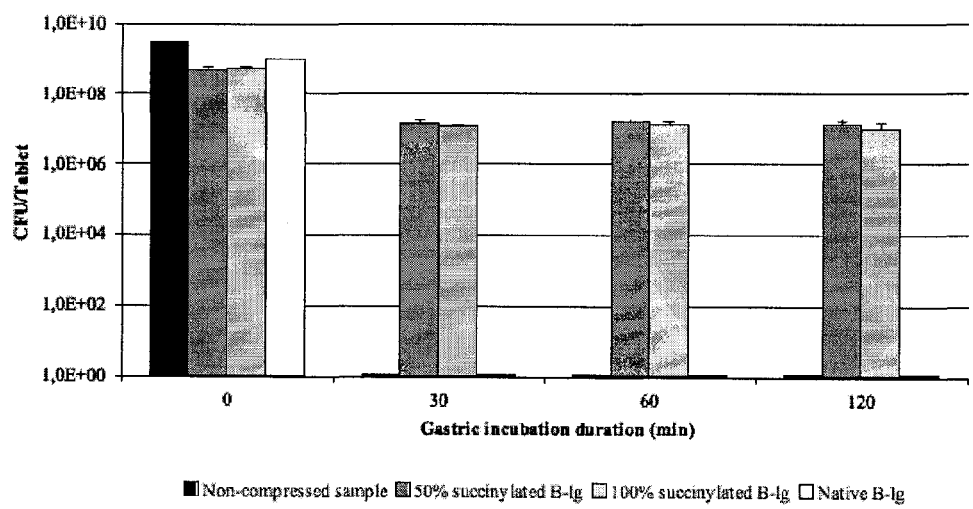
FIG. 14: Release profiles of a tablet comprising 10% *Bifidobacterium longum* (probiotic) and 90% succinylated β-Lactoglobulin (w/w) as a function of residence time in SGF.

FIG. 14 shows that B. longum HA-135 can not survive in SGF when non-compressed in a tablet. After a 30 minute incubation, no viable cell remained which corresponds to a 9 log decrease in the number of bacteria. The use of native β-lg as excipient did not allow to conserve viability of B. longum HA-135 either. The tablet was completely dissolved after 30 minutes in SGF and no viable bacteria remained. This 9 log cell death is therefore equivalent to what was observed for the lyophilized bacteria in powder form. In its native state, β-lg has no protective effect on gastric conditions.

Also shown in FIG. 14, a mixed system of B. longum HA-135 and succinylated β-lg (at 50 or 100%) did allow survival of $10^7$ CFU/tablet, which corresponds to only a 2 log reduction in viability ($10^9 \rightarrow 10^7$ CFU/tablet). This figure also shows that survival is maintained irrespective of incubation time in SGF.

Without wishing to be bound by theory, the different behavior between the modified protein and its native form can be explained by the presence of carboxyl groups that decrease the isoelectric point of the protein and thus decrease its solubility at low pH. The formation of a gel-like coating or layer on the surface of the tablet (therefore limiting solvent penetration) after being exposed to SGF solution, combined with the buffer properties of the succinylated protein matrix, are thus factors responsible for the protection and survival of B. longum HA-135. The slight mortality observed was associated to cells exposed to the solvent situated on the surface of the tablet, and did not benefit from the protective effect.

A particular attention was brought to the pH variations in the tablet during SGF incubation. To achieve this, colorimetric indicator (purple bromocresol) was mixed to the powders. Color variations of the tablets were followed as a function of incubation times.

Figure 15:
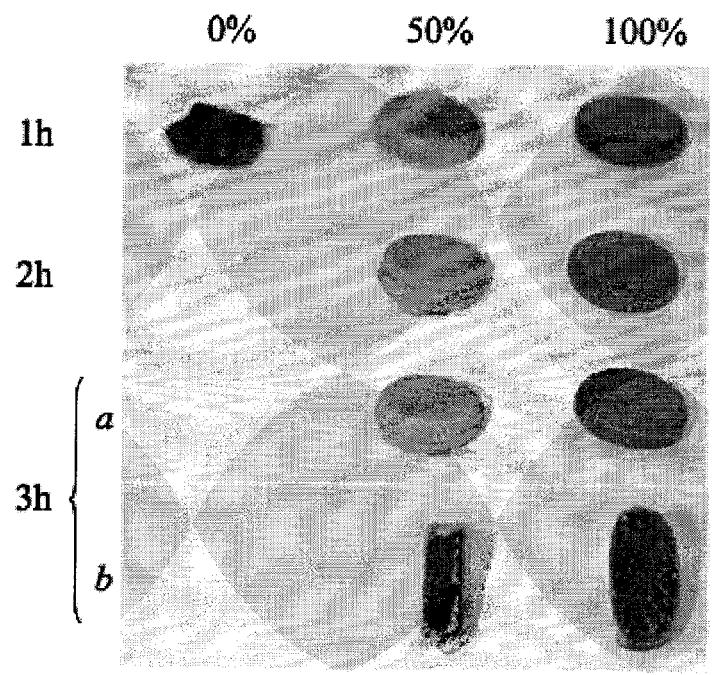
FIG. 15: Photographs showing color variations of tablets made up of succinylated β-lactoglobulin as a function of extent of succinylation and time of incubation in SGF.

FIG. 15 illustrates color variations for tablets made up of succinylated lactoglobulin as a function of succinylation and time of incubation in SGF. It can be seen from FIG. 15 that tablets made up of native proteins rapidly disintegrate. However, it seems that tablets made up of modified proteins are less eroded as a function of time. In addition, although the tablet surface changes color to orange-yellow indicating a pH lower than 5, the inside of the tablet remains blue/purple even after 3 hours of incubation. Consequently, the internal pH of the tablet tends to remain identical or above 6.5.

In conclusion, tablets made from protein modified at 50 and 100% allow a release targeted toward the intestine and a resistance to pH variations (buffer effect) explaining the low bacterial mortality after gastric passage.

Example 4

Delayed-Release of a Probiotic

In order to increase the number of bacteria brought to the intestine but also to evaluate the minimal quantity of excipient required to observe gastro-resistance, tablets were formulated with varying ratios of excipient:active ingredient. The initial content of tablets formed with 10, 20 and 40% of lyophilized bacteria as well as the remaining content after 60 minutes gastric incubation was determined. Tablets were made up of 400 mg (total) and were formed at 67 MPa, for 30 sec.

Figure 16:
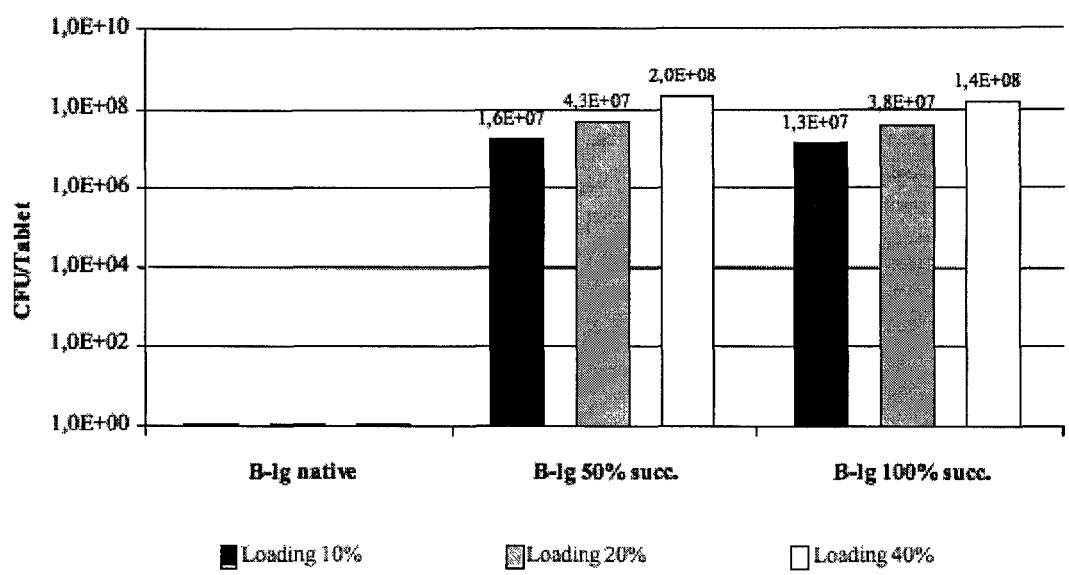
FIG. 16: Number of remaining viable cells (*Bifidobacterium longum*) after one hour of exposure to GSF in a tablet of succinylated β-Lactoglobulin as a function of % of bacteria vs. excipient (w/w)

FIG. 16 shows that increasing the ratio of lyophilized bacteria in the formulation results in an proportional increase of viable cells irrespective of whether the excipient: β-lactoglobulin, is native or succinylated. Thus, the number of viable cells doubles when the tablet content in bacteria goes from 10 to 20%, and again from 20% to 40%. These results are in agreement with those of Klayraung et al., (2009).

FIG. 16 also presents the survival achieved following gastric incubation as a function of tablet loading as well as different excipients used. In the case of tablet made with native β-lg, bacterial survival was nil, irrespective of the proportion of lyophilized bacteria included in the formulation. Tablets made up of 50% or 100% succinylated β-lg, behaved similarly. By incorporating 20% of lyophilized bacteria, the survival rate was 3× higher than with a load of 10%. At 40% loading, the increase was even higher: survival was 11× higher than with 10% load. Klayraung et al., (2009) have also realized that the percent survival in tablets was higher when the formulation contained a higher proportion of lyophilized bacteria. These authors explain their results by the fact that cell-cell interactions may improve the protection against environmental stress. In our present case, the explanation may rather come from the low solubility of the lyophilized bacteria, that, in combination with the low solubility of the excipient, has limited to a greater degree the solvent penetration inside the matrix and thus increased bacterial protection.

These results therefore indicate that it is possible to considerably increase the proportion of active ingredient in a tablet while maintaining, or even improving, the delayed-release properties of succinylated β-lg matrix in gastric medium. This indicates also that there is possibility to further improve the processability of the formulation by further adding other excipients or ingredients. The increase in loading of active ingredient at 40% has allowed to obtain an initial bacterial count of the order of $10^9$ CFU/tablet, which corresponds to threshold required by Regulatory Authorities concerning probiotics. Furthermore, this has allowed to increase the survival rate at $10^8$ CFU/tablet after a 60 minute gastric incubation.

Example 5

Figure 17A:
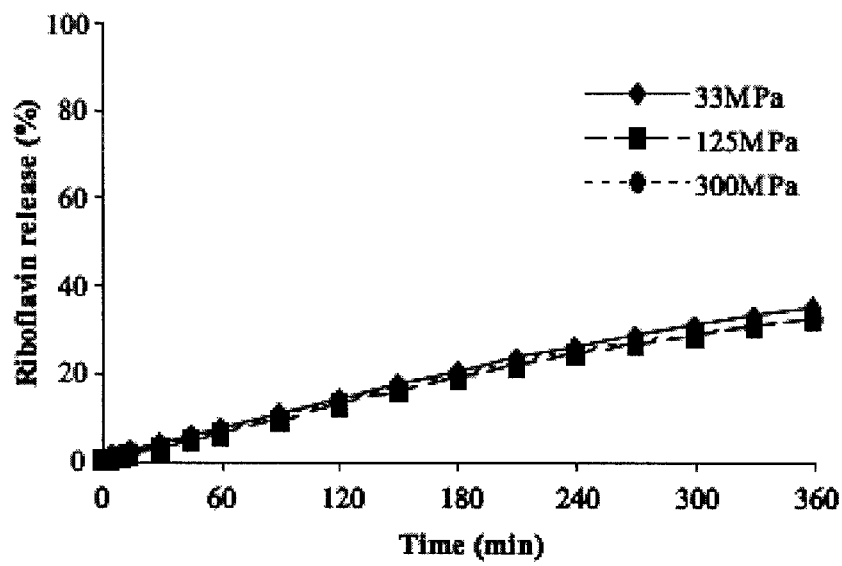
FIG. 17: Release profile of riboflavin in GSF from tablets made with β-Lactoglobulin (a) 50% succinylated and (b) 100% succinylated as a function of pressure used to form tablets. 33 MPa (1000 lbs) corresponds to the lower limit of the press. It seems that the pressure used to form the tablets does not impact on the release dynamics of the tablets.
Figure 17B:
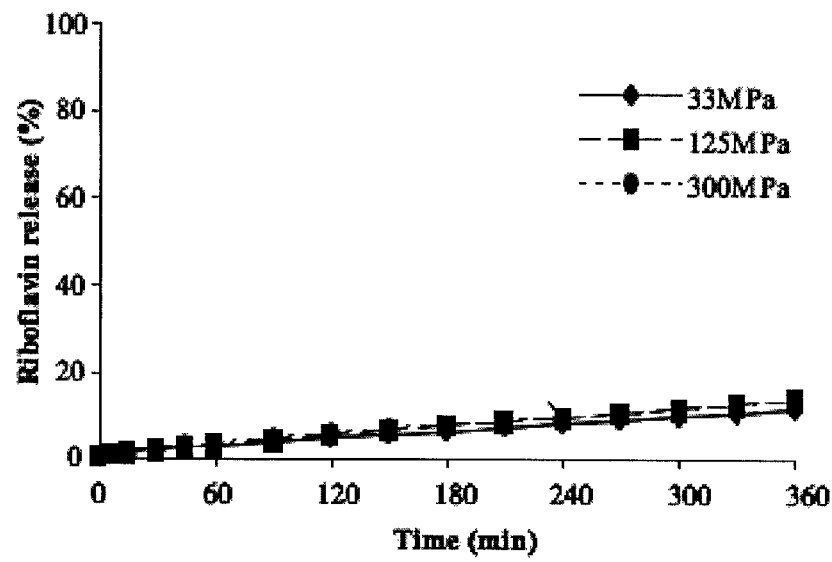

Release properties of tablets as a function of extent of modification (%) of the protein excipient have been studied in SGF and SIF (not shown) as a function of pressure applied during the formation of the tablets. FIG. 17 illustrates the release profiles obtained for riboflavin in simulated gastric conditions for proteins succinylated at 50% (a) and succinylated at 100% (b).

The same protocol was applied as previously for tablet formation. The compression time was 30 sec and compression force was of: 33, 125 and 300 MPa. Dissolution was also carried out as previously described.

It seems that, irrespective of the pressure applied in tablet formation, all tablets showed identical release properties. Consequently, gastro-resistance of the tablet is not dependent on the pressure applied during compaction. Only the extent of modification of the protein seems to influence the release properties: porosity of the tablet or its rigidity do not demonstrate any effect on gastro-resistance.

Example 6

Figure 18:
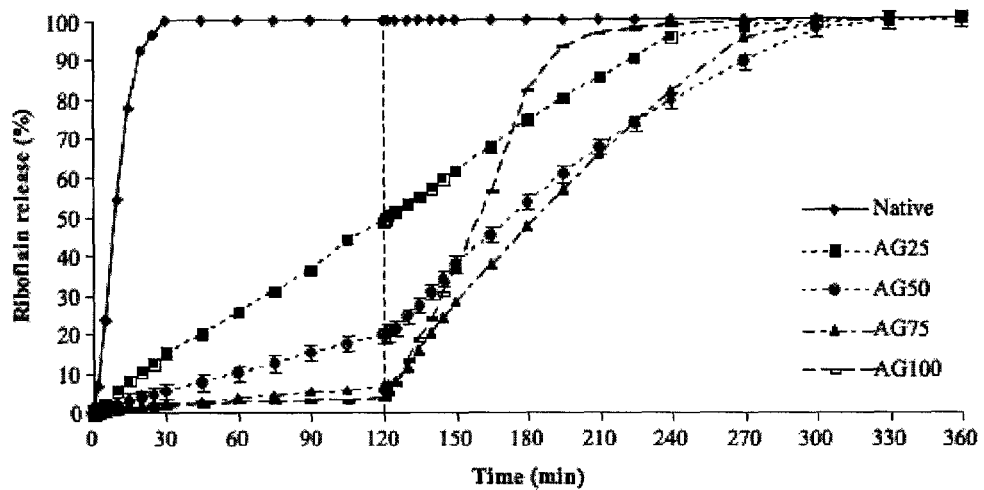
FIG. 18: Riboflavin release profiles obtained for β-lactoglobulin glutarylated at 0, 25, 50, 75 and 100% for residence time of 2 hours in SGF followed by 4 hours in SIF.

FIG. 18 illustrates release profiles obtained for tablets of Riboflavin mixed with β-lactoglobulin glutarylated at 0, 25, 50, 75 and 100% for residence time of 2 hours in SGF (the first 2 hours correspond to a gastric release whereas the following 4 hours simulate intestinal phase).

Figure 19:
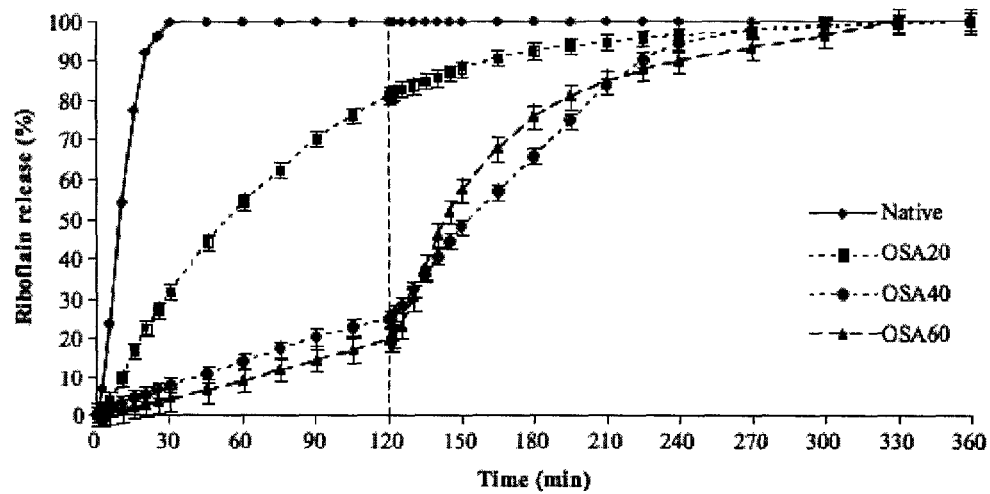
FIG. 19: Roboflavin release profiles obtained for tablets made up with β-lactoglobulin octenyl-succinylated at 0, 20, 40 and 60% for simulated gastric residence time of 2 hours followed by 4 hours in SIF.

FIG. 19 illustrate the release profiles obtained for tablets made up of Riboflavin mixed with β-lactoglobulin octenyl-succinylated at 0, 20, 40 and 60% for simulated gastric residence time of 2 hours followed by 4 hours in SIF.

As was observed with succinylated β-lactoglobulin tablets, an increase in the extent of modification (glutarylation or octenyl-succinylation) leads to a decrease in release in simulated gastric phase. The results is reversed in simulated intestinal phase (see level of the curves in linear zone).

Examples 3 to 5 shows that release profiles of the tablets and their gastro-resistance depends almost exclusively on the extent of modification of the protein used as excipient. No link having been established with porosity, rigidity of the tablet and gastro-resistance, it seems that the functionality of the system is ensured from the moment the modified protein is compressed, whatever the pressure and time used to achieve a solid form, such as a tablet.

CONCLUSION

The results suggest that tablets prepared from succinylated soy proteins or β-lactoglobulin have good properties as delivery devices: they delay drug release in simulated gastric fluid for both highly and insoluble molecules and favor it in simulated intestinal fluid. Moreover, assuming that gastric residence time is between 30 min (empty stomach) to about 4 h (ingestion of a nutritive meal) and considering that "classical" tablets enteric coating can be a long and costly process (Mc Ginity, 1989), it appears that proteins chemical modification constitutes a new interesting way to produce gastro-resistant tablets. This work underlines the potential of proteins (particularly food proteins) as pharmaceutical excipient for the conception of controlled-release tablets.

REFERENCES

Achouri A. et Zhang W., (2000), Effect of succinylation on the physicochemical properties of soy protein hydrolyzate, Food Research International, 34, 507-514.
Achouri A., Zhang W. et Shiying X., (1998), Enzymatic hydrolysis of soy protein isolate and effect succinylation on the functional properties of resulting protein hydrolyzates, Food Research International, 31, 617-623.
A. O. C. S., (1998), Official methods and recommended practices of the AOCS, 5$^{th}$ ed. Champaign, Ill.: The American Oil Chemists's Society Ba 11-65.
Arrondo J. L. R., Muga A., Castresana J., Goni F. M., (1993), Quantitative studies of the structure of proteins in solution by Fourier-transform infrared spectroscopy. Progress in Biophysics and Molecular Biology, 59, 23-56.
Chen L, Remondetto and Subirade M. 2006. Food proteins-based materials as nutraceutical delivery systems. Trends in Food Science & Technology, 17, 272-283.
Costa P., Sousa Lobo J. M., (2001), Modeling and comparison of dissolution profiles. European Journal of Pharmaceutical Sciences, 13, 123-133.
El-Adawy T., (2000), Functional properties and nutritional quality of acetylated and succinylated mung bean protein isolate, Food Chemistry, 70, 83-91.
Ellepola S. W., Choi S. M., Ma C. Y., (2005), Conformational study of globulin from rice (Oryza sativa) seeds by Fourier-transform infrared spectroscopy. International Journal of Biological Macromolecules, 37, 12-20.
Ewe K., Press A. G., Bollen S. et Sschuhn I., (1991), Gastric emptying of ingestible tablets in relation to composition and time of ingestion of meals studied by metal detector, Digestive Diseases and Sciences, 36, 146-152.
Gueguen Jacques, Subirade Muriel, Barbot Jacky and Schwenke Klaus Dieter. 1993. *Influence of the dissociation on the surface behaviors of oligomeric seed storage proteins: the example of pea legumin*, In: Food Proteins: Structure and Functionality, ed. K. D. Schwenke and R. Mothes, VCH Weinheim (FRG), 281-289.
Gruener L. et Ismond H., (1997), Effects of acetylation and succinylation on the physichochemical properties of the canola 12S globulin. Part I, Food Chemistry, 60, 357-363.
Health Canada, (2004). Food and drug regulations, Part B, division 16, table XIII.
Hermansson A-M. (1985), Structure of soya glycinin and conglycinin gels. J Sci Food Agric, 36, 822-832.
Huang Y., Huiqun Y., Chaobo X. (2007), pH-sensitive cationic guar gum/poly(acrylic acid) polyelectrolyte hydrogels: Swelling and in vitro drug release, Carbohydrate Polymers, 69, 774-783.
Hwang D-C., Damodaran S., (1996), Chemical modification strategies for synthesis of protein-based hydrogel. Journal of Agriculture and Food Chemistry, 44, 751-758.
Jackson M., Mantsch H., (1992), Halogenated alcohols as solvents for proteins: FTIR spectroscopic studies. Biochimica et Biophysica Acta, 1118, 139-143.
Kavanagh G. M., Ross-Murphy S. B., (1998), Rheological characterization of polymer gels. Progress in Polymer Science, 23, 533-562.
Klayraung, S., Viernstein H., Okonogi, S., Development of tablets containing probiotics: Effects of formulation and processing parameters on bacterial viability, International Journal of Pharmaceutics, 2009, 370, p. 54-60.
Lefèvre T., Subirade M., (2000), Molecular differences in the formation and structure of fine-stranded and particulate β-lactoglobulin gels. Biopolymers, 54, 578-586.
Martins V. B., Netto F. M. (2006), Physicochemical and functional properties of soy protein isolate as a function of water activity and storage. Food Research International, 39, 145-153.
McGinity J. W., (1989), Aqueous Polymeric Coatings for Pharmaceutical Dosage Forms, Marcel Dekker.
Meng G. T., Ma C. Y., (2001), Fourier-transform infrared spectroscopic study of globulin from *Phaseolus angularis* (red bean). International Journal of Biological Macromolecules, 29, 287-294.
Peppas N. A., Bures P., Leobandun W., Ichikawa H., Hydrogels in pharmaceutical formulations, Eur. J. Pharm. Biopharm. 50 (2000) 27-46.
Ritger P. L., Peppas N. A. (1987), A simple equation for description of solute release II. Fickian and anomalous release from swellable devices. Journal of controlled release, 5, 37-42.

Schwenke Klaus Dieter, Mothes Ralf, Zirwer Dietrich, Gueguen Jacques and Subirade Muriel. 1993. *Modification of the structure of 11S globulins from plant seeds by succinylation*, In: Food Proteins: Structure and Functionality, ed. K. D. Schwenke and R. Mothes, VCH Weinheim (FRG), 143-153.

Sezer A. D., Akbuga J. (1995), Controlled release of piroxicam from chitosan beads. International journal of pharmaceutics, 121, 113-116.

Simons, J.-W. F. A., Koster, H. A., Visschers, R. W., de Jongh, H. H. J. (2002) Role of calcium as trigger in thermal β-lactoglobulin aggregation. *Archives of Biochemistry and Biophysics*, 406, 143-152.

Singh M. P. et al., (1995), The effect of electrostatic charge interactions on release rates of Gentamicin from collagen matrices, Pharmaceutical research, 12, 1205-1210.

Subirade M & Chen L. 2008. Food protein derived materials and their use as carriers and delivery systems for active food components, in: Delivery and controlled release of boactives in foods and nutraceuticals, Woodhead Publishing Ltd, Cambridge. p. 251-271).

Subirade M., Gueguen J., Schwenke K. D. (1992), Effect of dissociation and conformational changes on the surface behavior of pea legumin, Journal of Colloid and Interface Science, 152, 442-454.

The United States Pharmacopoeial Convention. (2004), General Tests and Assays. USP Convention Inc., Rockville Md., 1-6.

The United States Pharmacopoeial Convention. (2004), Tests Solutions. USP Convention Inc., Rockville Md., 9-23.

The invention claimed is:

1. A pressed solid matrix comprising: an active ingredient in admixture with an excipient comprising a soy protein or a β-lactoglobulin wherein the soy protein and the β-lactoglobulin are chemically modified at between 25% to 100% of their available sites by way of: succinylation, acetylation, octenyl-succinylation or glutarylation, whereby said excipient when mixed with an active ingredient to form a mixture and then pressed in a solid matrix, causes a reduced swelling of the pressed solid matrix at acidic pH-and a delayed-release of said active ingredient upon oral ingestion.

2. The pressed solid matrix according to claim 1, selected from the group consisting of: a tablet, a granule, a pellet, a lozenge, a pill and a caplet.

3. The pressed solid matrix according to claim 2, wherein said excipient consists essentially of: succinylated soy proteins or succinylated β-lactoglobulin.

4. A method for preparing a pressed solid matrix comprising an active ingredient in admixture with a globular protein excipient wherein said globular protein is a soy protein or a β-lactoglobulin, said method comprising the steps of:
   a) chemically-modifying said globular protein at between 25% to 100% of its available sites by way of succinylation, acetylation, octenyl-succinylation or glutarylation;
   b) mixing said protein with the active ingredient to form a mixture; and
   c) pressing said mixture to form a solid matrix;
   whereby said excipient, when formulated in a pressed solid matrix, causes a reduced swelling of the pressed solid matrix at acidic pH and delays release of said active ingredient from said matrix when ingested orally by a subject.

5. The method as defined in claim 4, wherein step a) is carried out under conditions to modify the globular protein at a range of from 50% to 100% of its available sites.

6. The method according to claim 1, wherein said excipient is a soy protein.

7. The method according to claim 4, wherein said protein consists essentially of: succinylated soy proteins or succinylated β-lactoglobulin.

8. The method according to claim 4, wherein the pressed solid matrix is selected from the group consisting of: a tablet, a granule, a pellet, a lozenge, a pill, and a caplet.

9. The pressed solid matrix according to claim 1 wherein the soy protein or β-lactoglobulin is chemically modified at between 50% to 100% of its available sites.

10. The pressed solid matrix according to claim 1 wherein the soy protein or β-lactoglobulin is chemically modified at between 75% to 100% of its available sites.

11. The pressed solid matrix according to claim 1 wherein the soy protein or β-lactoglobulin is chemically modified at 100% of its available sites.

12. The pressed solid matrix according to claim 1 wherein the soy proteins or β-lactoglobulin is modified by succinylation at between 50% to 100% of its available sites.

13. The pressed solid matrix according to claim 1 wherein the soy proteins or β-lactoglobulin is modified by succinylation at between 75% to 100% of its available sites.

14. The pressed solid matrix according to claim 1 wherein the soy proteins or β-lactoglobulin is modified by succinylation at 100% of its available sites.

15. The method as defined in claim 7, wherein step a) is carried out under conditions to modify the globular protein at a range of from 50% to 100% of its available sites.

* * * * *

UNITED STATES PATENT AND TRADEMARK OFFICE
CERTIFICATE OF CORRECTION

| | |
|---|---|
| PATENT NO. | : 8,795,724 B2 |
| APPLICATION NO. | : 12/995891 |
| DATED | : August 5, 2014 |
| INVENTOR(S) | : Romain Caillard et al. |

It is certified that error appears in the above-identified patent and that said Letters Patent is hereby corrected as shown below:

ON THE TITLE PAGE:

ITEM (57) IN THE ABSTRACT:

| | |
|---|---|
| Line 4: | Replace -- succmylation -- with -- succinylation --. |
| Line 4: | Replace -- glytarylation -- with -- glutarylation --. |
| Line 7: | Replace -- protem-protem -- with -- protein-protein --. |
| Line 11: | Replace -- lactoglobulm -- with -- lactoglobulin --. |

IN THE 'REFERENCES CITED' ITEM (56) UNDER OTHER PUBLICATIONS:

| | |
|---|---|
| Page 2, Column 1, line 18, reads: | -- Guegen et al. 1993, "Influence f the dissociation on the surface --. |
| Should read: | -- Gueguen et al. 1993, "Influence of the dissociation on the surface --. |
| Page 2, Column 1, line 26, reads: | -- Hwang D.C. & Damodaran S., 1996, "Chemial modification strate --. |
| Should read: | -- Hwang D.C. & Damodaran S., 1996, "Chemical modification strate --. |
| Page 2, Column 2, lines 10 and 11, read: | -- changes on the surface behaviour of Pea Legumin," J. Collod Internface Sci., 152: 442-454. --. |
| Should read: | -- changes on the surface behaviour of Pea Legumin," J. Collod Interface Sci., 152: 442-454. --. |
| Page 2, Column 2, line 20, reads: | -- tion on the physichochemical properties of the canola 12S globulin", --. |

Signed and Sealed this
Fourteenth Day of April, 2015

Michelle K. Lee
*Director of the United States Patent and Trademark Office*

CERTIFICATE OF CORRECTION (continued)
U.S. Pat. No. 8,795,724 B2

| | |
|---|---|
| Should read: | -- tion on the physicochemical properties of the canola 12S globulin", --. |
| Page 2, Column 2, line 23, reads: | -- physiochemical properties of soy protein hydrozylate.", Food --. |
| Should read: | -- physicochemical properties of soy protein hydrozylate.", Food --. |
| Page 2, Column 2, line 32, reads: | -- new tablet excipient." European Journal of Pharmaceutics ans Biopharmaceutics, 69: 718-726. --. |
| Should read: | -- new tablet excipient." European Journal of Pharmaceutics and Biopharmaceutics, 69: 718-726. --. |

IN THE SPECIFICATION:

Column 1, line 65, replace -- pl -- with -- pI --.

Column 2, lines 8, 9 and 18, replace -- pl -- with -- pI --.

Column 3, lines 9 and 12, replace -- GSF -- with -- SGF --.

Column 3, line 22, replace -- Roboflavin -- with -- Riboflavin --.

Column 3, line 46, replace -- pl -- with -- pI --.

Column 4, lines 32 and 51, replace -- pl -- with -- pI --.

Column 5, lines 4, 7, 10, 13, 20, 26, 29, 31, 32, 36, 39, 42, 45, 51, 58, 61, 63, 64, replace -- pl -- with -- pI --.

Column 5, line 37, replace -- 3-Lactoglobulin -- with -- B-Lactoglobulin --.

Column 6, line 2, replace -- pl -- with -- pI --.

Column 7, line 1, replace -- phényléthylamines -- with -- phenylethylamines --.

Column 7, line 36, replace -- pl -- with -- pI --.

Column 7, line 37 (both instances), replace -- pl -- with -- pI --.

Column 12, lines 62, 63 and 64, replace -- pl -- with -- pI --.

Column 13, line 3, replace -- s-amino group -- with -- ε-amino group --.

Column 13, lines 14 and 20, replace -- pl -- with -- pI --.

Column 15, line 42, replace -- author authors -- with -- other authors --.